US006479281B1

(12) United States Patent
Göttlinger et al.

(10) Patent No.: US 6,479,281 B1
(45) Date of Patent: Nov. 12, 2002

(54) INFECTIOUS PSEUDOTYPED LENTIVIRAL VECTORS LACKING MATRIX PROTEIN AND USES THEREOF

(75) Inventors: Heinrich Göttlinger, Brookline, MA (US); Heide Reil, Braunschweig (DE); Anatoly Bukovsky, Bellevue, WA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/670,075

(22) Filed: Sep. 26, 2000

Related U.S. Application Data

(63) Continuation of application No. PCT/US99/07220, filed on Apr. 1, 1999.
(60) Provisional application No. 60/080,504, filed on Apr. 2, 1998.
(51) Int. Cl.[7] ................ C12N 15/867; C12N 15/63; C12N 15/64
(52) U.S. Cl. ............... 435/320.1; 435/455; 435/456; 435/457; 435/91.1; 435/325; 435/91.4; 424/93.1; 424/93.2; 424/93.6
(58) Field of Search ................ 435/320.1, 455, 435/456, 457, 91.1, 325, 91.4, 91.42; 424/93.1, 93.2, 93.6

(56) References Cited

U.S. PATENT DOCUMENTS 5,656,465 A 8/1997 Panicali et al.
5,665,577 A 9/1997 Sodroski et al.

OTHER PUBLICATIONS

John H. Elder et al, Feline Immunodeficiency Virus As A Model For Development Of Molecular Approaches To Intervention Strategies Against Lentivirus Infections, Advances In Virus Research, vol. 45.*
Geller, AI et al., J. Neurochem. 64: 487 (1995).
Geller, AI et al., Proc. Natl. Acad. Sci USA 90: 7603 (1993).
Legal Lasalle, Science 259: 988–90 (1993).
Davidson, et al., Nat. Genet. 3:219 (1993).
Yang, et al., J. Virol. 69: 2004 (1995).
Kaplitt, MG et al., Nat. Genet. 8:148 (1994).
Hunter, E., Semin. Virol. 5:71–83 (1994).
Wang, et al., Journal of Virology. vol. 67, No. 12, pp. 7067–7076 (1993).
Gonzalez, et al., Journal of Virology. vol. 70, No. 9, pp. 6384–6389 1996.
Dorfman, et al., Journal of Virology. vol. 68, No. 3, pp. 1689–1696, (1994).
Mammano, et al. Journal of Virology. vol. 69, No. 6, pp. 3824–3830 (1995).
Poeschla, et al. Proceedings of the National Academy of Sciences, U.S.A. vol. 93, pp. 11395–11399 (1996).
Wilk, et al. Virology. vol. 189, pp. 167–177 (1992).
Vzorov, et al., Virology. vol.. 221, pp. 22–33 (1996).
Reil, et al., The EMBO Journal. vol. 17, No. 9, pp. 2699–2708 (1998).
Kafri, et al., Journal of Virology. vol. 73, No. 1, pp. 576–584 (1999).
Poeschla, et al. Journal of Virology. vol. 72, No. 8, pp. 6527–6536 (1998).

\* cited by examiner

*Primary Examiner*—David Guzo

(57) ABSTRACT

Vector systems that encode viral proteins that will assemble into an infectious lentivirus particle having a deletion of the lentiviral matrix are described. In one embodiment the vectors encode a lentiviral envelope protein that contains a deletion of the cytoplasmic tail. In a second embodiment a heterologous envelope as compared to the lentivirus is used such as an envelope protein that targets an endocytic compartment.

26 Claims, 9 Drawing Sheets

INFECTIOUS PSEUDOTYPED LENTIVIRAL VECTORS LACKING MATRIX PROTEIN AND USES THEREOF

This application is a continuation of copending international application PCT/US99/07220, Apr. 1, 1999, which is hereby incorporated by reference, and which designated the U.S. The nonprovisional application designated above, namely application PCT/US99/07220, filed Apr. 1, 1999, claims the benefit of U.S. provisional application No. 60/080,504, filed Apr. 2, 1998.

The present invention was funded by National Institutes of Health grants AI29873, AI28691 (Center for AIDS Research), and CA06516 (Cancer Center), and the U.S. Government has certain rights thereto.

FIELD OF THE INVENTION

The present invention is directed to a replication competent lentiviral particle that lacks all or a portion of the matrix (MA) protein. Preferably, the particle is a pseudotyped lentiviral particle that contains an envelope protein that targets endocytic compartments, and the vectors that express the particles.

BACKGROUND OF THE INVENTION

In recent years considerable effort has been directed at applying in vivo gene therapy techniques. That term describes a wide variety of methods using recombinant biotechnology techniques to deliver a variety of different materials to a cell. These methods include, for example, vectors such as viral vectors, liposomes, naked DNA, adjuvant-assisted DNA, gene gun, catheters, etc. The different techniques used depend in part upon the gene being transferred and the purpose therefore. Thus, for example, there are situations where only a short-term expression of the gene is desired in contrast to situations where a longer term, even permanent expression of the gene is desired.

Vectors that have been looked at include both DNA viral vectors and RNA viral vectors. For example, DNA vectors include pox vectors such as orthopox or avipox vectors (see, e.g., U.S. Pat. No. 4,656,465), herpes virus vectors, such as herpes simplex I Virus (HSV) vector [Geller, A. I. et al., *J. Neurochem.* 64:487 (1995); Lim, F., et al., *DNA Cloning: Mammalian Systems*, D. Glover, Ed., (Oxford Univ. Press, Oxford, England) (1995); Geller, A. I. et al., *Proc. Natl. Acad. Sci.*, U.S.A. 90:7603 (1993); Adenovirus vectors [Legal Lasalle et al., *Sci.* 259–988 (1993); Davidson et al., *Nat. Genet.* 3:219 (1993); Yang et al., *J. Virol.,* 69:2004 (1995); and Adeno Associated Virus Vectors [Kaplitt, M. G., et al.]; *Nat. Genet.* 8;148 (1994)]. Retroviral vectors include moloney murine leukemia viruses (MMLV) and human immunodeficiency viruses (HIV) [See, U.S. Pat. No. 5,665, 577].

While much attention has been focussed on the use of viral vectors, particularly for in vivo therapy, for example, in somatic cell therapy or direct in vivo applications, the clinical testing, particularly large-scale clinical testing is still in its infancy with these vectors. Thus, it is not surprising that results from many of these early trials produces a mixed clinical picture. Nor is it surprising that improvements in viral vectors can still be made.

For example, a retroviral vector can be used to infect a host cell and have the genetic material integrated into that host cell with high efficiency. One example of such a vector is a modified moloney murine leukemia virus (MMLV), which has had its package sequences deleted to prevent packaging of the entire retrovial genome. However, that retrovirus does not transduce resting cells. Additionally, since many retroviruses typically enter cells via receptors, if the specific receptors are not present on a cell or are not present in large enough numbers, the infection is either not possible or is inefficient. Concerns have also been expressed as a result of outbreaks of wild-type viruses from the recombinant MMLV producing cell lines, i.e., reversions.

Recently, attention has focussed on lentiviral vectors such as those based upon the primate lentiviruses, e.g., human immunodeficiency viruses (HIV) and simian immunodeficiency virus (SIV). HIV vectors can infect quiescent cells in addition to dividing cells. Moreover, by using a pseudotyped vector (i.e., one where an envelope protein from a different species is used), problems encountered with infecting a wide range of cell types can be overcome by selecting a particular envelope protein based upon the cell you want to infect. Moreover, in view of the complex gene splicing patterns see in a lentiviruses such as HIV, multivaliant vectors (i.e., those expressing multiple genes) having a lentiviral core, such as an HIV core, are expected to be more efficient. Despite the advantages that HIV based vectors offer, there is still a concern with the use of HIV vectors in view of the severity of HIV infection. Thus, means for providing additional attenuated forms that are less likely to revert to a wild type virus are desirable.

Ultimately, the use of any of these vectors will require the ability to produce such a vector in large scale. Consequently, the method of attenuation and/or preventing reversion should be one that does not adversely affect the ability to have producer cells express large amounts of these vectors. Moreover, the method of attenuation should also not adversely affect the vector's ability to infect and be expressed in resting cells. Otherwise, one of the substantial advantages of using a lentiviral vector will be lost.

Replication-competent retroviruses contain a matrix (MA) protein which forms a submembrane layer in the mature virion. HIV-1 MA requires a myristylated N-terminus for membrane binding, and has been believed to be essential both for early and late steps of the virus life cycle.

The MA protein is a cleavage product of the polyprotein, Pr55$^{gag}$, which cleavage is the precursor for the internal structural proteins of the mature virion (Hunter, 1994). Processing of Pr55$^{gag}$ during virus maturation yields the capsid (CA), nucleocapsid (NC), and p6 proteins, in addition to MA.

Pr55$^{gag}$ is cotranslationally myristylated and targeted to the inner leaflet of the plasma membrane, where virus assembly occurs (Hunter, 1994). The assembling particle buds through the plasma membrane and thereby acquires a lipid membrane enriched in viral envelope (Env) glycoproteins. MA forms a spherical shell directly underneath the lipid membrane of the mature virion. CA forms the characteristic conical core, and NC is complexed with the genomic RNA within the core (Hunter, 1994).

SUMMARY OF THE INVENTION

Surprisingly, we have found that a lentivirus for example, HIV, feline immunodeficiency virus (FIV), or visna virus, can transduce both dividing and non-dividing cells in the absence of the entire MA or a portion thereof, if a myristylation anchor is provided.

The lentiviral virion (particle) is expressed by at least one vector containing a nucleic acid sequence encoding the lentiviral pol proteins necessary for reverse transcription and integration, operably linked to a promoter. There is also a nucleic acid sequence encoding the lentiviral gag proteins necessary for forming a viral capsid operably linked to a promoter. Preferably, this gag nucleic acid sequence is on a separate vector than the pol nucleic acid sequence. The gag sequence does not express a functional MA protein. This can be accomplished by inactivating the "gene" encoding the MA by additions, substitutions or deletions of the MA coding region. Preferably, this is done by deletion. Preferably, at least 25% of the MA coding region is deleted, more preferably, at least 50% is deleted, still more preferably, at least 60%, even more preferably at least 75%, still more preferably, at least 90%, yet more preferably at least 95% and most preferably the entire coding region is deleted.

A myristylation anchor (sequence) is required. Preferably, the myristylation sequence is a heterologous (i.e., non-lentiviral) sequence.

The vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301–319).

The vector(s) preferably do not contain a nucleic acid sequence from the lentiviral genome that expresses an envelope protein. Preferably, a separate vector contains a nucleic acid sequence encoding an envelope protein operably linked to a promoter. This env vector also does not contain a lentiviral packaging sequence. In one embodiment the env nucleic acid sequence encodes a lentiviral envelope protein. However, the env sequence is altered from the wild type sequence so that it encodes a truncated cytoplasmic tail. Preferably, 50% of the cytoplasmic tail is missing. More preferably, at least 75% is deleted, still more preferably at least 90% is deleted, even more preferably, at least 95% is deleted. Most preferably, the entire cytoplasmic tail is deleted.

In a more preferred embodiment, the env sequence encodes an envelope protein from a different virus such as an envelope protein that targets an endocytic compartment such as that of the influenza virus, VSV-G, alpha viruses (Semliki forest, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus).

The preferred lentivirus is a primate lentivirus [U.S. Pat. No. 5,665,577] or a feline immunodeficiency virus (FIV) [Poeschla, E. M., et al., *Nat. Medicine* 4:354–357 (1998)] The pol/gag nucleic acid segment(s) and the env nucleic acid segment will when expressed produce an empty lentiviral particle. By deleting the MA coding region, the possibility of a reversion to a wild type virus has been reduced.

A desired heterologous nucleic acid segment can be inserted into the empty lentiviral particle by a vector containing a nucleic acid segment of interest and a lentiviral packaging sequence necessary to package lentiviral RNA into the lentiviral particles. Preferably, the vector contains a 5' and 3' lentiviral LTR with the desired nucleic acid segment inserted between them. The nucleic acid segment preferably encodes a protein.

These vectors can be used to express large amounts of viral particles. The particles can be used in a variety of areas. For example, they can be used to generate an immune reaction, to transform a cell with a heterologous nucleic acid sequence and/or to deliver a nucleic acid sequence to a desired host cell.

Pseudotyped lentiviral particles such as HIV-1 particles which lacked the globular head of MA remained fully infectious for macrophages, indicating that MA is dispensable for nuclear import even in terminally differentiated cells.

BRIEF DESCRIPTION OF THE DRAWINGS

FIG. 2A shows restoration of Env protein incorporation through removal of the cytoplasmic domain of HIV-1 Env. HeLa cells were transfected with wild type provial DNA or with the indicated mutants, followed by metabolic labeling with [$^{35}$S]cysteine. Virions released during the labeling period were pelleted through sucrose, and virion lysates were immunoprecipitated with serum from a patient infected with HIV-1.

FIGS. 2B and 2C show replication kinetics of MA-deletion mutants in MT4 cells. Target cells were challenged with normalized virus stocks produced by transfected HeLa cells (FIG. 2B) or infected MT4 cells (FIG. 2C). An infectious dose corresponding to 15 ng p24 per $10^6$ target cells was used in each experiment. Virus production was monitored by measuring the release of RT activity into the culture supernatants.

FIG. 3A shows increased viral particle yield upon replacement of MA by a heterologous myristyl anchor. HeLa cells were transfected with proviral DNAs which differed only in gag. Lysates of virions released during metabolic labeling with [$^{35}$S]cysteine were directly analyzed by SDS-PAGE (left panel). Viral proteins expressed in the transfected cells were immunoprecipitated with patient serum (right panel). The bracket indicates the Env precursor and mature SU.

FIG. 3B shows MA is dispensable for the enhancement of particle release by Vpu. HeLa cells were transfected with proviral DNAs that harbor a wild type or a mutated gag gene and either an intact or a defective Vpu gene. Lysates of virions released during metabolic labeling with [$^\pm$S]cysteine were directly analyzed by SDS-PAGE.

FIG. 3C shows replication kinetics of passaged ΔMA/ΔCT virus. Virus recovered several weeks after infection of MT4 cells with HeLa derived ΔMA/ΔCT virus was passaged in fresh MT4 cells and RT activity released into the culture medium was measured. For comparison, the parental ΔCT virus was passaged in parallel. Infections were initiated using an amount of virus equivalent to 15 ng p24 per $10^6$ cells. P1, passage 1; P3, passage 3.

FIG. 3D shows protein content of wild type and mutant HIV-1 virions produced by infected MT4 cells (lanes 1 to 5). Lane 6 shows the protein content of HTLV-1 virions produced by MT2 cells. Lysates of virions released during metabollic labeling with [$^3$H]leucine were directly analyzed by SDS-PAGE.

FIG. 4A shows replication kinetics of variant isolates of the Δ8-87/ΔCT and ΔMA/ΔCT mutants which could be serially passaged in CEMx174 cells. Infections were initiated with CEMx174-derived mutant or wild type virus corresponding to 150 ng p24 per $10^6$ cells.

FIG. 4B shows the analysis of particle- and cell-associated viral proteins. Lysates of virions released from infected CEMc174 cells during labeling with [$^{35}$S]cysteine were directly analyzed by SDS-PAGE (left panel). Cell-associated viral proteins were immunoprecipitated with patient serum (right-panel).

FIGS. 5A and 5B show comparison of budding structures and extracellular particles produced in the presence or absence of MA. The arrowheads in FIG. 5B point to clearly visible surface projections on a MA-deficient budding structure.

FIG. 5C shows massive budding into intracellular membrane compartments in the absence of the MA core domain. Bars indicate length of 100 nm.

FIG. 6A shows mutations found in the gag gene of the replication-competent R0 recombinant.M$_{STC}$, 15-amino-acid peptide introduced to provide a heterologous myristyl anchor and processing site (see FIG. 1).

FIG. 6B shows the replication kinetics of variants of the MA-less mutant ΔMA/ΔCT which harbor the changes illustrated in FIG. 6A. MT4 cells were challenged with normalized virus stocks produced by transfected HeLa cells. An amount of virus equivalent to 75 ng per $10^6$ target cells was used. Virus replication was monitored by measuring RT activity in the culture supernatants.

FIG. 6C shows the effect of compensatory changes in gag on CA processing. Lysates of [$^{35}$S]methionine-labeled virions produced by transfected HeLa cells were directly analyzed by SDS-PAGE.

Figure 7A:
FIGS. 7A–7D show an analysis of the efficiency of the early phase of virus transmission in the absence of MA sequences.
Figure 7B:
Figure 7C:
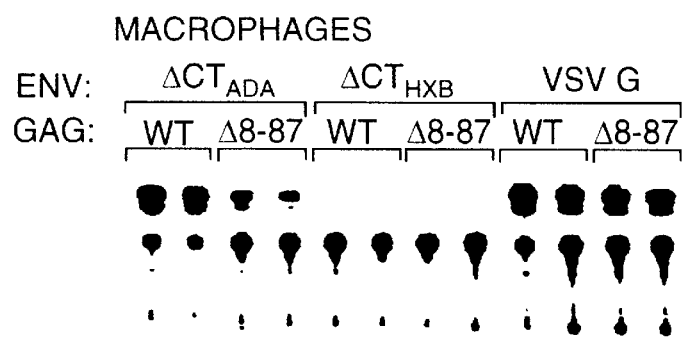
Figure 7D:
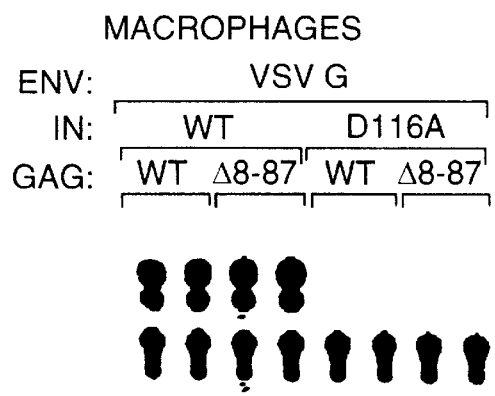

The T lymphoid cell lines MT4 (FIG. 7A) and Jurkat (FIG. 7B), or primary human monocyte-derived macrophages (MDM) from 2 different donors (FIGS. 7C and 7D) were exposed to recombinant viruses containing the indicated Gag and Env proteins. Recombinant viruses used in (FIG. 7D) contained either an active or inactive integrase (IN). The results of CAT assays performed on the target cell lysates are shown. All experiments were performed in duplicate.

DETAILED DESCRIPTION OF THE INVENTION

The lentiviral virion (particle) is expressed by at least one vector containing a nucleic acid sequence encoding the lentiviral pol proteins necessary for viral protein expression operably linked to a promoter. There is also a nucleic acid sequence encoding the lentiviral gag proteins necessary for reverse transcription and integration operably linked to a promoter. Preferably, this gag nucleic acid sequence is on a separate vector than the pol nucleic acid sequence encoding the pol protein. The use of separate vectors for the various "genes" further reduces the chance of a reversion to wild-type. For example, it is preferable that the pol sequences encoding different pol proteins are also on separate vectors.

The gag sequence does not express a functional MA protein. This can be accomplished by inactivating the "gene" encoding the MA by additions, substitutions or deletions of the MA coding region. Since the MA is part of the gag gene and as expressed, is processed from the precursor protein, when referring to a MA gene (or coding region), we are only referring to that portion of the entire gag gene that encodes the MA subunit. Preferably, the inactivation is accomplished by deletion. Preferably, at least 25% of the MA coding region is deleted, more preferably, at least 50% is deleted, still more preferably, at least 60%, even more preferably at least 75%, still more preferably, at least 90%, yet more preferably at least 95% and most preferably the entire coding region is deleted.

The MA has a myristylation anchor and that myristylation anchor (sequence) is required. Preferably, the myristylation sequence is a heterologous (i.e., non-lentiviral) sequence. Src, MARCKS (myristolylated alanine-rich C kinase substrate). ARF (ADP-ribosylation factor), recovering and related EF-hand calcium-binding proteins (visinin neurocalcin and others), and non-lentiviral gag proteins (e.g., Moloney murine leukemia virus, Mason-Pfizer monkey virus).

The MA-deleted viruses consistently exhibit an increased ability to release extracellular virus particles, indicating there is no requirement for the globular domain of MA for stable membrane association. Surprisingly, deleting the globular head of MA, which harbors the putative MA nuclear localization signal (NLS), also permits the early steps of the lentiviruses replication cycle in macrophages.

MA has been believed to be essential for efficient and effective replication of retroviruses including lentiviruses because of the general conservation of the protein. Additionally, the globular head harbors a putative NLS, which was believed necessary both for efficient membrane association of gag, and for nucleic import and integration of the viral genome in non-dividing terminable differentiated cells such as macrophages.

The MA provides an N-terminal plasma membrane targeting domain (Kräusslich & Welker, 1996). Myristylation of the MA domain at a N-terminal glycine residue is required for the efficient association of $Pr55^{gag}$ with the plasma membrane and, as a consequence, for virus particle formation and replication (Göttlinger et al., 1989, Byrant & Ratner, 1990)). Several MA mutants have been described which are myristylated but are primarily targeted to intracellular membrane compartments. Consequently, additional determinants in MA are likely to contribute to the plasma membrane targeting of $Pr55^{gag}$. Similarly, myristylation is not believed sufficient for stable membrane attachment, since the membrane-binding energy contributed by the insertion of myristic acid into a lipid bilayer is only 8 kcal/mol. Indeed, biochemical and genetic studies indicate that a highly conserved N-proximal cluster of basic residues in HIV-1 MA mediates binding to acidic membrane phospholipids. It was shown that the first 31 amino acids of HIV-1 MA, which include both the N-terminal myristyl anchor and the N-proximal basic cluster, form an autonomous membrane targeting domain. A role of basic residues in membrane targeting is also supported by the three-dimensional structure of HIV-1 MA, which is composed of a globular "head" formed by four α-helices and a C-terminal fifth α-helix which projects away from the core domain (Massiah et al., 1994; Matthews et al., 1994; Hill et al., 1996). The globular head, whose structure is highly conserved among widely divergent retroviruses, forms trimers in all known MA crystal forms. N-proximal basic residues are found on the upper surface of the trimer where they would be appropriately positioned to interact with acidic phospholipid head groups (Hill et al., 1996).

The membrane affinity of the MA protein lentivirus such as HIV-1 appears to be regulated. For example, while the membrane binding signal in MA appears to be exposed in the context of Pr55$^{gag}$, it appears hidden in mature MA (Zhou & Resh, 1996). This is believed to allow MA to dissociate from the membrane in order to assist in early steps of the replication cycle (Bukrinsky et al., 1993; Gallay et al., 1995 a). In contrast to oncoretroviruses, lentiviruses such as HIV-1 can productively infect non-dividing cells, which requires the active transport of the viral nucleoprotein complex through the nucleopore (Weinberg, et al., 1991; Bukrinsky et al., 1992; Lewis et al., 1992). HIV-1 preintegration complexes have been reported to contain several karyophilic components including MA, Vpr, which independently promote the nuclear import of the viral genome. (Bukrinsky et al., 1993; Heinzinger et al., 1994; Gallay, et al., 1997). In MA, the aforementioned NLS was found to reside in the N-proximal basic cluster, which is also considered to be required for the efficient membrane association of Pr55$^{gag}$ (Bukrinsky et al., 1993). Although viruses carrying substitutions in the MA NLS replicated efficiently in dividing cells, they did not do so in growth-arrested cells or terminally differentiated monocyte-derived macrophages (MDM). The lack of efficient replication in non-dividing cells is consistent with a role of MA in translocating the HIV-1 nucleoprotein complex through the intact nuclear membrane (Bukrinsky et al., 1993; Heinzinger et al., 1994; vonSchwedler et al., 1994).

Further phosphorylation on serine and tyrosine residues releases MA from the membrane, enabling it to perform its nuclear import function (Bukrinskaya et al., 1996). In particular, phosphorylation of MA and C-terminal tyrosine residue has been shown to be crucial for the nuclear import of the viral preintegration complex and for virus replication in MDM (Gallay et al., 1995a and 1995b). For example, mutating the C-terminal tyrosine to phenylalanine did not affect virus replication in dividing cells, but it caused a profound defect in HIV-1 nuclear import and replication in terminally differentiated macrophages. There have been some conflicting results reported by others which indicate that neither the N-proximal basic cluster nor the C-terminal tyrosine of MA contribute selectively to HIV-1 replication in macrophages (Freed et al., 1995; Freed et al., 1997; Fouchier et al.; 1997).

The vector(s) preferably do not contain a nucleic acid sequence from the lentiviral genome that expresses an envelope protein. Preferably, a separate vector contains a nucleic acid sequence encoding an envelope protein operably linked to a promoter. This env vector also does not contain a lentiviral packaging sequence.

In one embodiment the env nucleic acid sequence encodes a lentiviral envelope protein. However, the env sequence is altered from the wild type sequence so that it encodes a truncated cytoplasmic trail. Preferably, 50% of the cytoplasmic tail is missing. More preferably, at least 75% is deleted, still more preferably at least 90% is deleted, even more preferably, at least 95% is deleted. Most preferably, the entire cytoplasmic tail is deleted.

In a more preferred embodiment, the env sequence encodes an envelope protein from another virus such as an envelope protein that targets an endocytic compartment such as that of alpha viruses (Semliki forest virus, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus). Preferably influenza virus or VSV, more preferably VSV-G.

While MA is essential for the incorporation of Env glycoprotein spikes into nascent viral particles (Yu et al., 1992b; Dorfman et al., 1994) in a wild-type lentivirus, we have been able to create these recombinant particles. The Env glycoproteins are dispensable for particle production per se, but their incorporation is required for the formation of infectious virions. Small alterations throughout the globular domain of HIV-1 MA blocked the incorporation of autologous Env protein, but not that of amphotropic murine leukemia virus (A-MLV), a widely divergent oncoretrovirus (Freed & Martin, 1995; Mammano et al., 1995). A deletion which removed about four-fifth of HIV-1 MA still allowed the functional incorporation of A-MLV Env protein. However, these pseudotyped mutant particles retained only about 10% of the infectivity of pseudotyped wild type particles during a single round of virus transmission in dividing cells (Wang et al., 1993). This is in stark contrast to the present particles which retain an infectivity at least 50% that of the wild-type particle, more preferably, at least about 75%, still more preferably, at least about 85%, even more preferably, at least about 90%, and most preferably, at least about 95% of the wild type in the corresponding cell. Although not wishing to be bound by theory, we believe the inability of HIV-1 MA mutants to incorporate the autologous Env glcoprotein complex can be attributed to the size of the cytoplasmic domain of the transmembrane glycoprotein, which is much larger in HIV-1 than in oncoretroviruses such as A-MLV. A second-site mutation which essentially removed the cytoplasmic tail of HIV-1 TM fully restored the incorporation of the autologous Env protein complex into HIV-1 MA mutants (Freed & Martin, 1995; Mammano et al., 1995). Additionally, the second-site mutation also restored the ability of mutants with small alterations in MA to replicate in MT4 cells (Mammano et al., 1995), a human T cell line in which the Env cytoplasmic tail is not required for HIV-1 replication (Wilk et al., 1992).

The present vector system can be used to package a wide range of desired nucleotide segments, preferably a RNA segment, into an empty lentiviral particle because of the large genomes of lentiviruses, packaging vector. In addition, the use of promoters and enhancers can also significantly add to the length of an insert. Preferably, the system is used with multiple genes (i.e., multivalent genes). Moreover, by deleting a significant portion of a protein that was believed to be essential, MA, the chance of recombination and/or reversion to a wild-type virus, is further reduced. Accordingly, the system of the present invention provides a significant advantage over currently available vectors by allowing for inserts that can contain a number of promoters and genes and that can be used to transfect resting cells as well as dividing cells.

A desired heterologous nucleic acid segment can be inserted into the empty lentiviral particle by a vector containing a nucleic acid segment of interest and a lentiviral packaging sequence necessary to package lentiviral RNA into the lentiviral particles. Preferably, the vector contains a 5' and 3' lentiviral LTR with the desired nucleic acid segment inserted between them. The nucleic acid segment preferably encodes a protein.

Preferably, an origin of DNA replication (ori) which is recognized by the viral replication proteins and enzymes is also present. This vector permits packaging of desired nucleotide inserts in the pseudotyped particles. This vector is sometimes referred to as the packaging vector. This packaging vector is used to package any desired heterologous nucleic acid sequence, preferably a RNA sequence, into the particle. Preferably, the packaging vector contains (a) a promoter sequence operably linked to at least one heterologous nucleic acid sequence and (b) at least one sequence sufficient to permit transcription and processing of mRNA, the translation of which results in an expression protein. Still more preferably, this vector contains an intervening sequence following the promoter sequence. And even more preferably the processing sequence is a polyadenylation sequence. For example, the heterologous sequence can encode any desired protein, preferably, a therapeutic protein. It can also encode antisense DNA, RNA or a desired immunogen, such as an antigenic protein. It can encode specific peptide sequence that will generate an immunogenic reaction. Such a peptide sequence is typically at least about 6 amino acids in length.

The vector(s) is prepared so that none of the nucleotide segments used will contain a functional packaging site containing sequence, except for the packaging vector.

The other vector(s), e.g. the lentiviral gag and pol vector (s), and the envelope vectors do not contain nucleotides from the lentiviral genome that package lentiviral RNA, referred to as the lentiviral packaging sequence. In HIV this region corresponds to the region between the 5' major splice donor and the gag gene initiation codon (nucleotides 301–319).

The packaging sequence can be excluded from the vector (s) by any of a variety of techniques well known to the person of ordinary skill in the art. For example, one can simply delete the entire sequence. Alternatively, one can delete a sufficient portion of a sequence to render it incapable of packaging. An alternative strategy is to insert nucleotides into such a site to render it non-functional. Most preferably, one will delete the site entirely to prevent homologous recombination.

Accordingly, the lentiviral vectors can express the desired viral proteins, but because the packaging site has been removed, the resultant RNA segment will not have packaging sequences that will cause that RNA to be packaged into the lentiviral particles, and the recombinant virus will not be able to replicate and infect other cells.

The lentiviral vectors can also contain sequences encoding desired lentiviral regulatory proteins such as Tat, Rev, etc. If RRE and CAR sequences are included in the gene, the inclusion of sequence encoding Rev is necessary, unless the virus is expressed in the cytoplasm. These regulatory sequences can be on the other lentiviral vectors (e.g., gag vector, pol vector, or env vector), or on their own lentiviral vector.

The heterologous nucleotide sequence can encode a wide variety of proteins such as a therapeutic protein, i.e., one that compensates for an inherited or acquired deficiency. Examples of therapeutic proteins include neurotransmitter biosynthetic enzymes, e.g., tyrosine hydroxylase for the treatment of Parkinson's disease, neurotrophic factors including neurotrophins, e.g., nerve growth for the treatment of Alzheimer's disease, one can also use nerve growth factor receptor and the trk receptor; hypoxanthine-guanine porphoribosyl transferase (HGPRT) for the treatment of Lesch Nyhan disease; 3-hexosaminadase α chain for the treatment of tay Sachs disease; insulin for the treatment of diabetes. Receptors can also be prepared, e.g. the nerve growth factor receptor, the trk receptor, etc. Because the insert can be large, it is possible to encode a series of different proteins. For example, one can encode a series of proteins that form a receptor-ligand complex.

Other proteins include, for example, signal transmission enzymes, e.g., protein kinase c; transcription factors, e.g., c-fos, NF-Kβ; oncongenes, e.g., erbB, erbB-2/neu, ras; neurotransmitter receptors, e.g. glutamate receptor, dopamine receptor, etc.

The heterologous nucleotide sequence can also encode antisense molecules (DNA or RNA). These molecules can be used to regulate gene expression associated with a particular disease. The antisense molecules are obtained from a nucleotide sequence by reversing the orientation of the coding region with regard to the promoter. Thus, the antisense RNA is complimentary to the corresponding mRNA. For review of antisense science see Green, et al., Ann. Rev. Biochem. 55:569–597 (1986), which is herein incorporated by reference. The antisense sequence can contain modified sugar phosphate backbones to increase stability and make them less sensitive to RNA sensitivity. Examples of the modifications are described by Rossi, et al., Pharmacol. Ther. 50(2):245–354 (1991).

The heterologous nucleotide sequence is preferably operably linked to a promoter sequence capable of directing transcription of the sequence in a desired target cell. Lentiviruses such as the primate lentiviruses contain the Tat regulatory protein. This protein will transactivate a protein operably linked to a TAR element. The TAR element is present in the 5' LTR of the primate lentivirus. Thus, the expression of heterologous protein can be enhanced by transactivation. The LTR also contains a promoter. However, that promoter in the absence of transaction is relatively ineffective. Thus, the use of other promoters and enhancers is typically preferred. The promoter can be a promoter such as the SV40, CMV, HSV-1 IE, IE 4/5 or RSV (Rous sarcoma virus) promoters). Others include Srα-promoter (a very strong hybrid promoter composed of the SV40 early promoter fused to the R/U5 sequences from the HTLV-ILTR), tetracycline-regulatable promoters, tissue-specific promoters (e.g., alpha-fetoprotein promoter; and rhodopsin promoter for photoreceptor-targeted expression). Other promoters capable of directing transcription of the heterologous sequence in a specific target cell can also be used. For example, if the target cell is a neuronal cell, a promoter such as the neuron specific enolase promoter (Forss-Petter, et al., (1986)) can be used. The ray tyrosine hydroxylase (TH) promoter can support cell type specific expression in the midbrain (Song, et al., (1995). Furthermore, the use of inducible promoters or other inducible regulatory sequences, which are well known in the art, in some embodiments are preferred. For example, one could use a tar sequence operably linked to a gene encoding a desired protein if one is targeting an HIV infected cell. In such a system the tat protein produced by such an infected cell will transactivate the expression of the gene operably linked.

In order to minimize the possibility of a recombination event between the packaging vector and the lentiviral vector generating a wild type lentivirus, it is desirable that the package vector has a minimal degree of homology with the nucleotide segments encoding the particle vector. Preferably, one would use different promoters in these different vectors. These goals can be accomplished by a variety of means known in the art based upon the present disclosure.

Alternatively or in combination with the above approach of reducing homology, one can alter the sequence of a gene from the lentivirus segment so that it does not encode a functional protein. As used herein "functional" means a protein having a wild-type activity.

Any lentivirus can be used, including primate lentiviruses (such as HIV or SIV), FIV, CAEV, visna virus, and equine infectious anemia virus. The preferred lentivirus is a primate lentivirus [U.S. Pat. No. 5,665,577] or a feline immunodeficiency virus (FIV) [Poeschla, E. M., et al., *Nat. Medicine* 4:354–357 (1998)] The pol/gag nucleic acid segment(s) and the env nucleic acid segment will when expressed produce an empty lentiviral particle. By deleting the MA coding region, the possibility of a reversion to a wild type virus has been reduced.

Depending upon the particular purpose for the particles one can use known techniques to alter the lentivirus segment to inactivate genes that encode proteins present in the particle which cause certain effects. For example, inactivating those proteins that enhance replication, e.g., rev and/or tat. Vpu affects infectivity. Nef also affects the virus. In some embodiments to reduce the chance of virulence deletions of nef are preferred as it has been reported that nef appears to be required for efficient replication in vivo (based on the SIV mac model).

Cells can be transfected by the present vectors to prepare the viral particle. One can prepare the vectors in vitro, one would then harvest the particles, purify them and inject means by means well known in the art. More preferably one would purify the particles and then use those to infect the desired cells.

These vectors can be used to express large amounts of viral particles. One preferred use is in preparing particle producer cell lines. This requires transfecting a cell with the particle vector system described herein, the packaging vector, and culturing the cell line under conditions and time sufficient to express the viral proteins, which then form the particles. Thereafter, the particles can be purified by known techniques with care taken to insure that the structure of the particle is not destroyed. The particles can be used in a variety of areas. For example, they can be used to generate an immune reaction, to transform a cell with a heterologous nucleic acid sequence and/or to deliver a nucleic acid sequence to a desired host cell.

Pseudotyped lentiviral particles such as HIV-1 particles which lacked the globular head of MA remain fully infectious for macrophages, indicating that MA is dispensable for nuclear import even in terminally differentiated cells.

One can prepare transient or stable cell liners that express the lentiviral particles by standard techniques based upon the present teaching.

Thereafter, if a stable cell lines is desired one can screen for those cells that have been stably transfected by standard technique. In some embodiments it is the stable producer cell lines that are then transfected by the packaging vector.

Such stable producer cell lines are a preferred source for obtaining packaged particles.

The particle of the present invention can be used to deliver heterologous DNA to a target cell. The target cell may be in vivo, in vitro or ex vivo. The target cell can be a dividing or preferably a quiescent cell. Quiescent cells include nonmitotic or postmitotic cells. The preferred nonmitotic cell is a macrophage. The target cells also include cells of the nervous system, e.g., neural or neuronal cells. Preferred quiescent or slowly dividing target cells include glia cells, myocytes, hepatocytes, pneumocytes, retinal cells, and hematopoietic stem cells. Pancreatic islet cell are also a preferred target.

Introduction of the viral particle carrying the heterologous gene to be delivered to the target cell may be effected by any method known to those of skill in the art. For example, catheters, injection, scarification, etc. For example, stereotaxic injection can be used to direct the viral particles to a desired location in the brain. Stereotaxic surgery is performed using standard neurosurgical procedures (Pellegrino and Cushman, (1971)). Additionally, the particles can be delivered by intracerebroventricular ("icv")infusion using a minipump infusion system, such as a SynchroMed Infusion System. A recent method based on bulk flow, termed convection, has also proven effective at delivering large molecules to extended areas of the brain and may be useful in delivering the viral particle to the target cell (Bobo et al., (1994); Morrison et al., (1994)). Other methods can be used including catheters, intravenous, parenteral, intraperiotoneal and subcutaneous injection, oral or other known routes of administration.

One would inject a sufficient amount of the separate vectors or preferably the packaged viral particles to obtain a serum concentration in the tissue containing the target cell of the therapeutic protein ranging between about 1 pg/ml to 20 μg/ml. More preferably between about 0.1 μg/ml to 10 μg/ml. Still more preferably, between about 0.5 μg/ml to 10 μg/ml.

For example, solid dose form that can be used for oral administration include capsules, tablets, pills, powders and granules. In such solid dose forms, the active ingredient, i.e., empty virus particle, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings to release the particles over a predetermined time period.

For parenteral administration, one typically includes sterile aqueous or non-aqueous solutions, suspensions or emulsions in association with a pharmaceutically acceptable parenteral vehicle. Examples of non-aqeuous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispering agents. They may be sterilized by, for example, filtration through a bacterial-retaining filter, by incorporating sterilizing agents into the composition, by irradiating the compositions, etc., so long as care is taken not to inactive the virus particle. They can also be manufactured in a medium of sterile water or some other sterile injectable medium before use. Further examples of these vehicles include saline, Ringer's solution, dextrose solution and 5% human serum albumim. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably about 3 mg/ml to about 10 mg/ml.

Efficient replication of a lentivirus, particularly a primate lentivirus such as HIV, can be obtained in the absence of large portions or even of all of MA. MA-deleted viruses were unable to incorporate wild type HIV-1 Env protein. This inability can be alleviated by reducing the cytoplasmic tail such as by a second-site mutation which removed the large cytoplasmic domain of Env. The second-site mutation also allowed efficient HIV-1 replication in the absence of the entire globular domain of MA. Removing all of MA and instead inserting a heterologous myristylation signal produces a vector that can replicate efficiently after the acquisition of compensatory changes in gag. As discussed below, even HIV envelopes can be adapted to permit efficient replications by removing the HIV Env cytoplasmic tail. While the HIV Env cytoplasmic tail is typically required for effective HIV replication, this is not always the case. For example, in MT4 cells the cytoplasmic tail of Env is not needed for efficient HIV-1 replication. However, it is still required for the productive infection of other cells. Although MT4 cells harbor HTLV-1 proviral DNA, no particles containing HTLV-1 Gag were released, ruling out the possibility that the MA protein of HTLV-1 substituted for that HIV-1. Moreover, MA deletion mutants which possess a broader host range despite the absence of Env cytoplasmic tail sequences can be obtained by forced passage in non-permissible cells. These observations indicate that HIV-1 can adapt to the absence of Env cytoplasmic tail sequences in a way which allows replication in different cell types. Furthermore, these results exclude the possibility that the presence of HTLV-1 proviral DNA is a requirement for the spread of HIV-1 lacking MA.

The finding that HIV-1 can replicate and infect even in the total absence of MA was unexpected, since MA is a major structural protein which is found in all replication-competent retroviruses. One previous study showed that the second half of the RSV MA protein is dispensable for viral particle formation and infectivity. However, even small deletions in the N-terminal half of RSV MA completely abolish virus budding. Moreover, other RSV MA mutants produced wild type levels of particles but were unable to infect permissive cells, which was interpreted as evidence for a second critical function of MA in addition to its role in assembly. In the case of HIV-1, relatively small alterations throughout MA often allowed particle formation but prevented virus replication. Although the globular domain of MA is known to be critical for the accommodation of the long cytoplasmic tail of HIV-1 Env, certain deletions near the C terminus of MA which allowed Env protein incorporation nevertheless severely impaired virus infectivity.

We found that a deletion within the globular domain of MA prevents virus replication even after an Env incorporation defect is corrected. However, virus replication can be restored through the removal of additional MA residues, indicating that the presence of a defective MA domain rather than a requirement for MA per se was responsible for the replication defect caused by the less extensive deletion. Changes in CA allow replication in the total absence of MA. They are selected primarily to improve Gag processing rather than to compensate for the loss of a function associated with MA. An additional change in NC preferably is made to compensate for the loss of cis-acting elements in the MA coding sequence which increase the efficiency of RNA encapsidation.

The cytoplasmic tail of HIV-1 Env, although important for replication in most CD4-positive cells, was not required for efficient entry. For example, we assessed the infectivity of MA-deleted virions for a variety of target cells. In most cell lines tested, the early phase of virus replication was not or only moderately affected by the absence of the globular head of MA. The ability of the mutant particles to infect primary human PBMC and MDM from different donors varied somewhat, but was reduced by no more than fifteen-fold. No defect in infectivity for primary target cells is seen when the >8–87 particles were pseudotyped with an endocytic envelope such as VSV G protein rather than a HIV Env C-terminally truncated protein. The effect of VSV G is not due to a general enhancement of virion infectivity, because particles formed by wild type Gag are at least as infectious for primary target cells when complemented with C-terminally truncated HIV-1 Env rather than VSV G. While HIV-1 Env promotes direct fusion of the viral envelope with the plasma membrane in a pH-independent manner, internalization of HIV-1 particles pseudotyped with an endocytic envelope such as VSV G occurs via receptor-mediated endocytosis. For example, it can be blocked by inhibitors of endosomal acidification. While MA may help to overcome a barrier to viral entry through the plasma membrane, we have found that in the absence of MA this barrier can be circumvented by using an Env that changes the route of entry.

The globular head of MA is believed to contain a basic-type NLS which is critical for the import of the viral preintegration complex into the nucleus of non-dividing cells such as MDM. While disruption of the MA NLS had no effect on HIV-1 replication in proliferating MT4 cell cultures, it impaired replication in MDM, particularly in the absence of Vpr, a second nucleophilic virion component. Some recent studies failed to provide supporting evidence for a role of the N-proximal basic region of MA in post-entry nuclear import.

We have found that HIV-1 particles lacking both Vpr and the globular head of MA, when pseudotyped with VSV G, were as infectious for MDM as particles which lacked only Vpr. Since the transfer of CAT activity to MDM was absolutely dependent on the presence of a functional integrase, out findings indicate that the removal of the globular head of MA does not affect post-entry events up to integration.

MA is also believed to be crucial for late steps of the replication cycle. Certain single amino acid charges in MA profoundly reduce particle production, even if the stability of $Pr55^{gag}$ or its N-terminal myristylation are not affected. However, some studies in dividing cells have shown that large deletions which removed most of MA were tolerated with only minor effects on the efficiency of particle formation. Intriguingly, we have found that large deletions in MA invariably exhibit an increased capacity to form viral particles. A particularly pronounced increase in particle yield was observed when the entire MA domain was deleted and replaced by the myristylated N-terminus of an oncoprotein such as the oncoprotein $p60^{v\text{-}src}$. However, significant increases were also seen when the autologous myristylation signal was retained. The increased capacity of MA deletion mutants to form extracellular particles is particularly evident at low Gag expression levels. Of note, the mutants lacked the N-proximal basic region in MA which has been implicated in Gag membrane binding. According to a model proposed by Zhou et al., the basic region in the globular head of MA interacts with acidic phospholipids and thereby strengthens the interaction between Gag and the inner leaflet of the plasma membrane. The present invention does not exclude the possibility that the basic region confers specificity to the interaction of Gag with cellular membranes, but demonstrates that this region is dispensable for the stable membrane association of Gag. Indeed, even deletion mutant which essentially retained only the N-terminal myristyl anchor of MA yielded more particles than the wild type construct, indicating that myristic acid alone is sufficient to stably attach the remainder of the Gag polyprotein to the plasma membrane.

Although not wishing to be bound by theory, we believe that our observation that large deletions in MA increased particle yields may be explainable by the recently proposed myristyl switch hypothesis. According to this hypothesis, the N-terminal myristate can be sequestered by MA and would be available for membrane binding only after a conformational change which leads to its exposure. Our results are consistent with the possibility that Gag membrane binding and, as a consequence, particle production are increased in the absence of the globular domain of MA because the myristyl moiety can no longer be sequestered and is therefore constitutively exposed. This is supported by recent findings that smaller deletions within α-helical regions that make up the globular domain caused dramatic increases in the membrane binding of MA. Also, several of these deletions caused significant increases in viral particle yield. A myristyl switch mechanism could conceivably have evolved to ensure the selective targeting of Gag to the plasma membrane. One would then expect that constitutive exposure of the myristyl group should lead to non-selective membrane binding, which may explain the tendency of MA deletion mutants to bud into intracellular membrane compartments.

MA has been shown to interact with the cytoplasmic domain of the HIV-1 Env protein in vitro, and it has been proposed that this specific interaction directs Env into assembling virions. However, efficient Env incorporation can be achieved even in the absence both of its cytoplasmic domain and of MA. Thus, the propensity of Env to selectively associate with budding particles cannot be explained solely as a consequence of a specific interaction with MA. The function of the cytoplasmic domain of Env remains unclear, particularly since this domain is not required for efficient entry into a variety of target cells. It remains possible that the cytoplasmic domain has a role in virus morphogenesis which is cell type-dependent or which is obscured if the viral structural proteins are overexpressed in transfected cells.

The MA-deleted virions described can be used as fusion-competent lipid vesicles which contain a viral core. The remarkable replication potential of these structures is such that they can be used to create large scale producer cell lines. The resultant virions can be purified intact and introduced into a permissive cellular environment, as they remain fully infectious. Thus, they can be used as gene delivery vehicles.

The present invention is further illustrated by the following Examples. These Examples are provided to aid in the understanding of the invention and are not construed as a limitation thereof.

EXAMPLES

Plasmids

The parental HIV-1 provirus used in this study, HXBH10, is a vpu$^+$ variant of the infectious HXB2 molecular clone. HXBH10 encodes a C-terminally truncated Vpr protein which was reported to be unable to substituted for the nuclear import function of MA in macrophages. HXBH10ΔCT, a variant of HXBH10 with a premature termination codon in place of codon 713 of env. and HXBH10Δ envCAT, a derivative with a deletion in env and a CAT gene in place of nef, have been described. In-frame deletions in the MA coding regions of HXBH10, HXBH10ΔCT, and HXBH10Δ envCAT were generated by recombination of previously described MA mutants. In each case, two foreign codons specifying Ser-Art were inserted in place of the deleted MA codons. To generate the Δ1–126 mutation, the first nine codons of the HIV-1 gag gene were replaced by those for Rous sarcoma virus src (which specify the sequence (SEQ ID NO:1) Met-Gly-Ser-Ser-Lys-Ser-Lys-Pro-Lys), followed by codons specifying Ser-Arg to create a XbaI site. This was achieved by site-directed mutagenesis using a 74-mer (sense orientation: 5'-GGAGGCTAGAAG GAGAGAGATGGGTAGCAGCAAGAGCAAGCCTAA G TCTAGAGGGGGAGAATTAGATCGATGGG-3') (SEQ ID NO:2) and single stranded DNA from pSK$^+$ gag as a template. The XbaI site was then used for recombination with the XbaI site generated by the previously described N126 R mutation in MA. The ΔMA mutation, which was predicted to substitute the sequence Met-Gly-Ser-Ser-Lys-Ser-Lys-Pro-Lys-Thr-Val-Ser-Phe-Asn-Phe (SEQ ID NO:3) for MA, was generated by site-directed mutagenesis using a 88-mer (sense orientation: 5'-GGAGGCTAGAAGGAG AGAGATGGGTAGCAGCAAGAGCAAGCCTAAGA CAGT AAGCTTTAATTTCCCTATAGTGCAGAACATC CAGGGG-3') (SEQ ID NO:4). The Asp116 Ala mutation in the integrase coding region was generated by site- directed mutagenesis using the oligonucleotide 5'-CAATACATACCGCGAATG GCAGC-3' (SEQ ID NO:5) and single-stranded DNA from pGEMgag-pol. The mutation was transferred into HXBH10Δ envCAT on a PflMI fragment (nt 3491–5302) in exchange for the wild type fragment.

The pEnv-$_{HXB2}$ plasmid, an expresser for the HIV-1$_{HXB2}$ env gene products, was generated by inserting a SalI-XhoI fragment from pSVIIIenv into pBJ5stop. The pEnv$_{HXB2}$ΔCT derivative, which expresses a truncated HIV-1$_{HXB2}$ Env that lacks the 144 C-terminal amino acids of the cytoplasmic domain, was obtained by replacing a KpnI-XhoI fragment (nt 6347–8900) in pEnv$_{HXB2}$ by the corresponding fragment from HXBH10ΔCT. The pEnv$_{ADA}$ΔCT construct, an expressor plasmid for C-terminally truncated HIV-1$_{ADA}$ Env, was created by replacing a KpnI-BsmI fragment (nt 6347–8054) in pEnv$_{HXB2}$Δ by an equivalent fragment from the macrophage-tropic isolate ADA. The pHCMV-G plasmid expressing the VSV G protein was obtained from Theodore Friedmann.

Cells

HeLa cells were grown in Dulbecco's modified Eagle's medium supplemented with 10% fetal bovine serum. The T lymphoid cell lines MT4, MT2, C8166, SupT1, CEM-SS, and Jurkat clone E6-1, and the T-B cell hybrid CEMx174 were maintained in RPMI 1640 medium with 10% fetal bovine serum. Human PBMC were isolated from the blood of normal donors by Ficoll-Hypaque density gradient centrifugation. Monocytes were purified from PBMC by adherence to plastic. The purification procedure typically yielded more than 95% CD14$^+$ cells. Monocyte-derived macrophages (MDM) were obtained by culturing purified monocytes for two weeks in RPMI 1640 and 10% fetal bovine serum without additional cytokines. PBMC were stimulated for 24 hrs with phytohemagglutinin (1 $\mu$g/ml) and maintained in RPMI 1640 containing 10% fetal bovine serum and 10% of a human interleukin-2 preparation (Hemagen Diagnostics, Columbia, Md.).

Transfections and Infections

HeLa cells were transfected by a calcium phosphate precipitation technique as previously described. To determine the ability of virions to initiate a productive infection, supernatants were passed through 0.45-$\mu$m-pore-size filters, and equivalent amounts of $^{32}$P-RT activity measured were used to inoculate $3\times10^6$ target cells in 2 ml culture medium. Following overnight incubation, the cells were washed and resuspended in 5 ml culture medium. Viral replication was monitored by measuring $^{32}$P-RT activity or, in some experiments, $^3$H-RT activity in the culture supernatants.

Viral Protein Analysis

Transfected or infected cells were metabolically labeled for 12 hr with [$^{35}$S]cysteine or [$^3$H]leucine (50 $\mu$Ci/ml). Labeled cells were lysed in RIPA buffer (140 mM NaCl/8 mM $Na_2HPO_4$/2 mM $NaH_2PO_4$/1% Nonidet P-40/0.5% sodium deoxycholate/0.05% SDS), and viral proteins were immunoprecipitated with serum from an individual infected with HIV-1 and subjected to SDS-polyacrylamide gel electrophoresis (SDS-PAGE). Viral particles released during the labeling period were pelleted through sucrose cushions (in PBS) for 90 min at 4° C. and 26,000 rpm in a Beckman SW 28 rotor. Pelleted virions were lysed in RIPA buffer and viral proteins were either directly analyzed by SDS-PAGE or immunoprecipitated prior to electrophoresis.

Molecular Cloning of Revertant Sequences

Total DNA was purified from MT4 cells five days postinfection with the QIAamp Blood Kit (Quiagen, Chatsworth, Calif.). Proviral segments were amplified with primer pairs flanking unique restriction sites, and then used to substitute equivalent fragments in $_{[src]}$MA/ΔCT. The primer pairs were Pr5'702 (5'-GAC GCAGGACTCGGCTTG-3') (SEQ ID NO:6) and Pr3'2438 (5'-TAGCTTTATGTCCACAG ATTTCTATGAG-3') (SEQ ID NO:7), Pr5'2345 (5'-TCTATTAGATACAGGAGCAGATG ATACAG-3') (SEQ ID NO:8) and Pr3'5834 (5'-GCTCTAGTCTAGGAT CTACTGGCTC-3') (SEQ ID NO:9), or Pr5'5732 (5'-GGATACTTGGGCAGGAGTGGAAG-3') (SEQ ID NO:10) and Pr3'9414 (5'-TCCCTTGTAGCAAG CTCGATGTCA-3') (SEQ ID NO:11). The restriction enzyme sites used to generate recombinant proviruses were BssHII and BclI, BclI and SalI, or SalI and BspEI.

Env-Complementation Assay

To produce recombinant virions, HeLa cells were cotransfected with wild type or mutant HXBH10 envCAT and an expression plasmid for HIV-1 Env (pSR HXB2, pSR HXB2 CT, pSR ADA CT), VSV G protein (pHCMV-G), or empty vector as previously described. Equivalent $^{32}$P-RT units of filtered supernatants (corresponding to approximately 25 ng p24$^{gag}$) were used to inoculate 2×10$^6$ target cells in 6-well dishes. The cells were incubated for 3 to 5 days, lysed, and assayed for CAT activity. To facilitate a comparison of relative infectivities, lysate from cells that had been infected with recombinant virus with an intact MA protein was serially twofold diluted with lysate from uninfected cells.

Electron Microscopy

Infected MT4 cells were fixed in 2.5% glutaraldehyde (in culture medium) for 30 min, sedimented at 200× g, and overlaid with 2.5% glutaraldehyde in PBS. Cell pellets were post-fixed in 1% osmium tetroxide, embedded in agar, treated with 2% uranyl acetate, and finally embedded into Epon. Ultrathin sections were poststained with lead citrate and examined in a Zeiss 10 A transmission electron microscope at 60 kV. Measurements of virus dimensions were taken from the negatives of electron micrographs recorded at a 40,000-fold magnification using a magnifying device with a scale grid. Particles were measured only when the full length of the mature core was apparent. Viral particle size was evaluated by calculating the mean of the minimum and maximum diameters for each virion.

RESULTS

Figure 1:
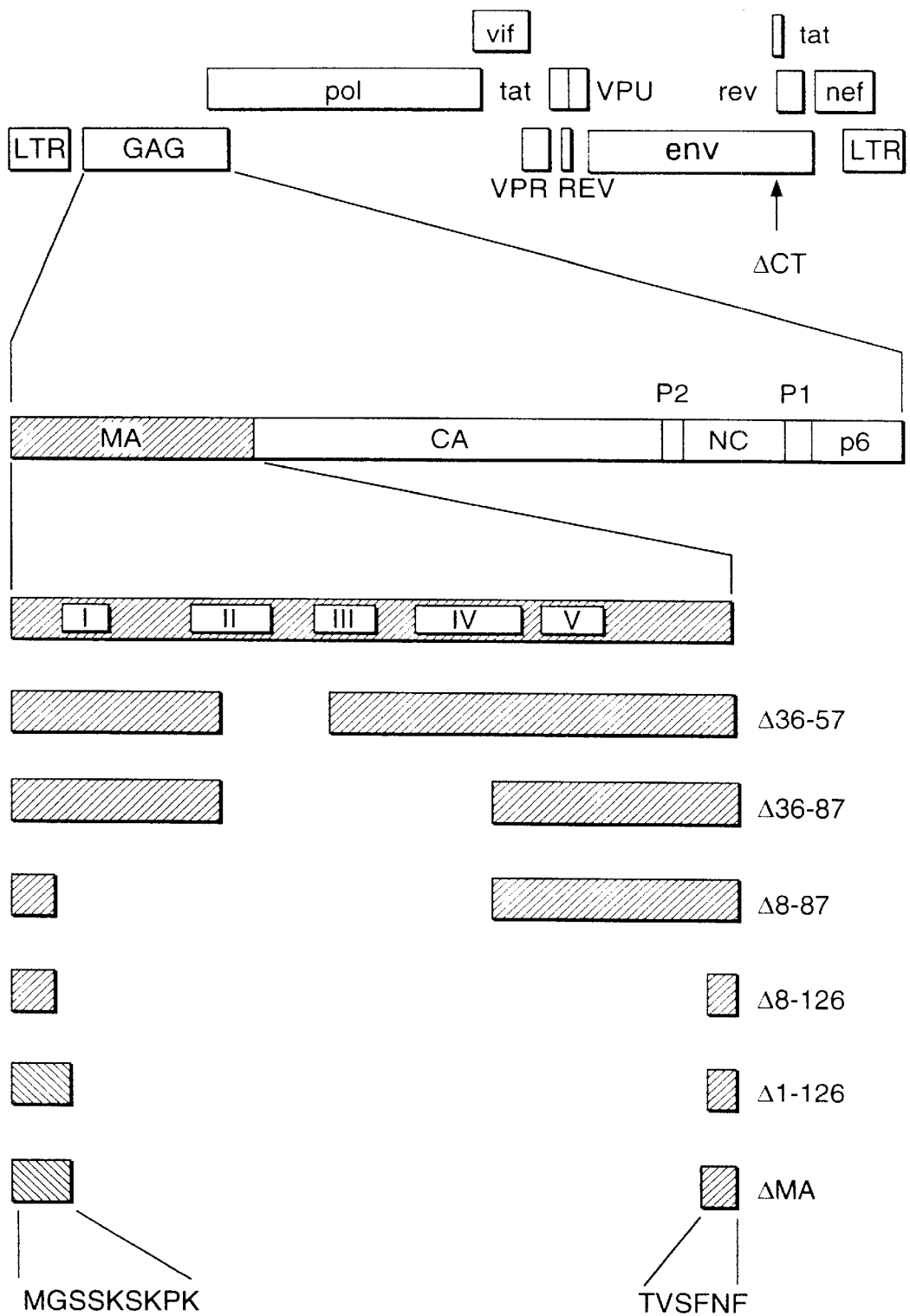
FIG. 1 shows a schematic representation of MA deletion mutants. The white and black boxes within the expanded view of MA indicate the positions of α-helics T through V and the two $3_{10}$ helices, respectively. Other shadings indicate heterologous sequences. The position of the ΔCT mutation, which introduces a premature termination codon into Env, is also indicated.
Figure 2A:
FIGS. 2A–2C show Env incorporation and virus replication in the absence of the globular core of MA.

Incorporation of Truncated but not Full-length Env in the Absence of the Globular Core of MA We deleted 119 of the 132 codons for MA from a proviral clone of HIV-1 (FIG. 1). The very N-terminus of MA was retained to provide a myristylation signal, which is required for particle formation. As shown in FIG. 2A, the Δ8-126 mutant not only retained the ability to form viral particles after transfection into HeLa cells, but produced particles in amounts that exceeded those obtained with the wild type construct. In repeated experiments, the Δ8-126 mutant yielded about 2- to 4-fold more viral particles than the parental virus as judged from the intensity of gag- and pol-encoded protein bands in the particulate fractions. Immunoprecipitation from the cell lysates showed that the Δ8-126 mutation did not increase viral protein expression (data not shown), indicating that the deletion instead improved the efficiency of viral particle assembly or release.

The protein composition of Δ8-126 mutant particles indicated that the large deletion in MA allowed efficient processing of the remainder of the Gag polyprotein. However, the mutant particles contained small amounts of a novel protein which migrated slower than mature CA, presumably as a consequence of slightly retarded processing at the MA/CA cleavage site. As expected, Δ8-126 particles lacked MA and Env, while both were readily detectable in wild type particles (FIG. 2A).

To explore whether the mutant was able to incorporate C-terminally truncated Env, the Δ8-126 deletion was combined with the ΔCT mutation (Mammano et al., 1995). The second-site mutation introduced a premature termination codon into env, which resulted in a truncated cytoplasmic domain that retained only 7 out of 151 amino acids. As shown in FIG. 2, the levels of gp120 surface glycoprotein relative to those of CA in Δ8-126/ΔCT particles were at least as high as in wild type virions. In addition, a significant amount of the C-terminally truncated Env precursor was incorporated. The absolute amounts of Env in Δ8-126/ΔCT particle preparations exceeded those in wild type particle or ΔCT particle preparations, consistent with the increase in particle yield caused by the Δ8-126 mutation. These results established that the entire globular core of MA is dispensable for the incorporation of C-terminally truncated HIV-1 Env protein.

Efficient Virus Replication in the Absence of the Globular Core of MA

The ΔCT mutation can neutralize the replication defect caused by a 3-amino-acid deletion in MA. Variants of the ΔCT mutant were generated which lack MA codons 36 to 57 (mutant Δ36-57/ΔCT) or MA codons 36 to 87 (Δ36-87/ΔCT). Virus stocks were prepared by transfection of the double mutants into HeLa cells and used to infect MT4 cells after normalization for reverse transcriptase (RT) activity. MT4 cells were used as target cells because the ΔCT mutation has only a moderate effect on HIV-1 replication in this cell line. Virus replication was monitored over time by measuring RT activity in the culture supernatants. Interestingly, while the Δ36-57/ΔCT mutant did not yield a spreading infection, the Δ36-87/ΔCT mutant replicated, although with a significantly delayed kinetics (data not shown).

Figure 2B:
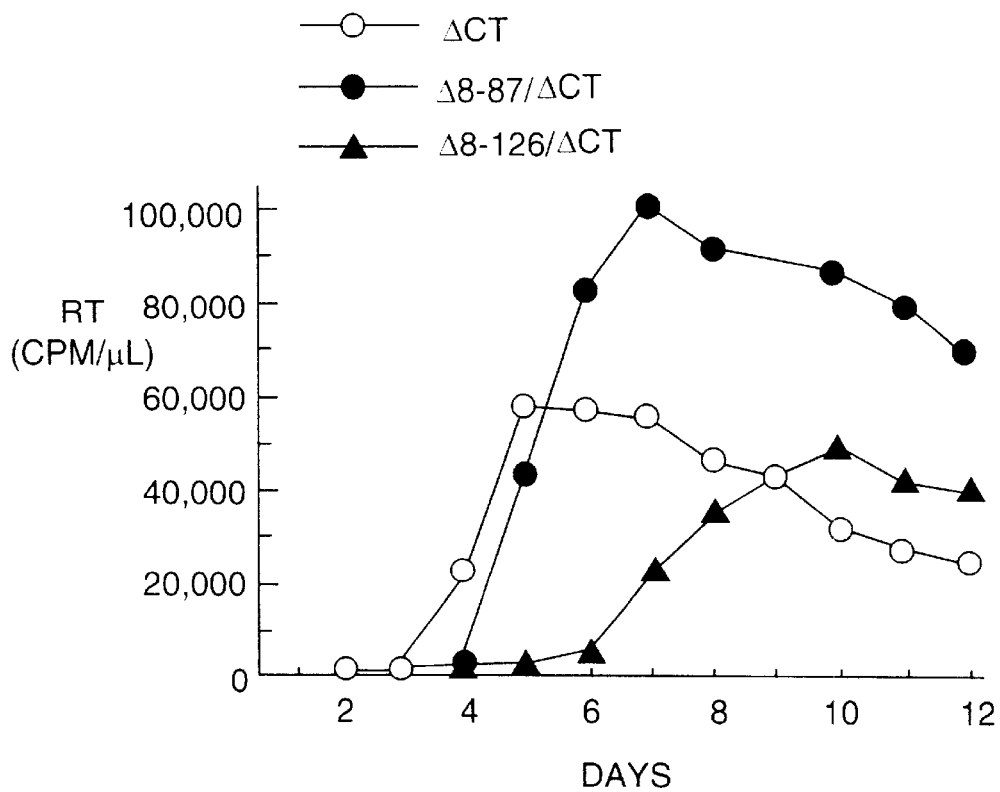
Figure 2C:
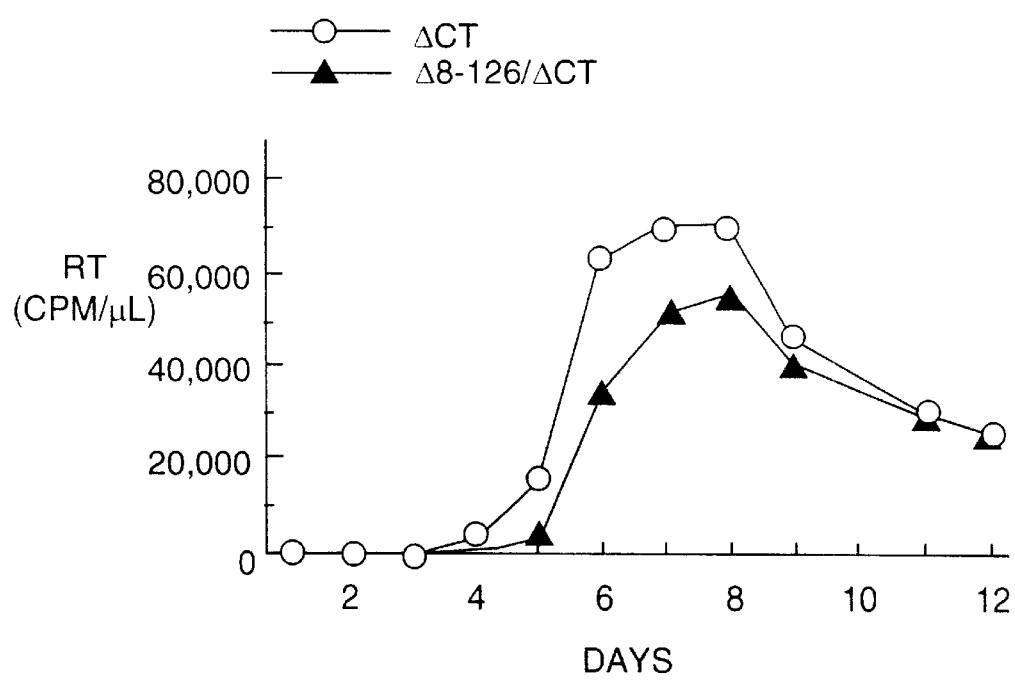

Remarkably, the deletion of an additional 28 residues from the N-terminus of MA, which yielded the Δ8-87/ΔCT mutant, accelerated virus replication to levels which approached those observed with the parental ΔCT construct (FIG. 2B). Even the Δ8-126/ΔCT mutant, which lacks about 90% of MA, replicated with only moderately delayed kinetics relative to the ΔCT mutant (FIGS. 2B and 2C). In several independent experiments, the Δ8-87/ΔCT mutant yielded higher peak levels of RT activity than the parental ΔCT construct. This observation probably reflects differences in cytopathogenicity, because cell numbers dropped more rapidly in cultures infected with the parental ΔCT virus (data not shown). As expected, the Δ8-87 and Δ8-126 mutations prevented virus replication in the presence of a wild type env gene (data not shown).

Figures 3A, 3B:
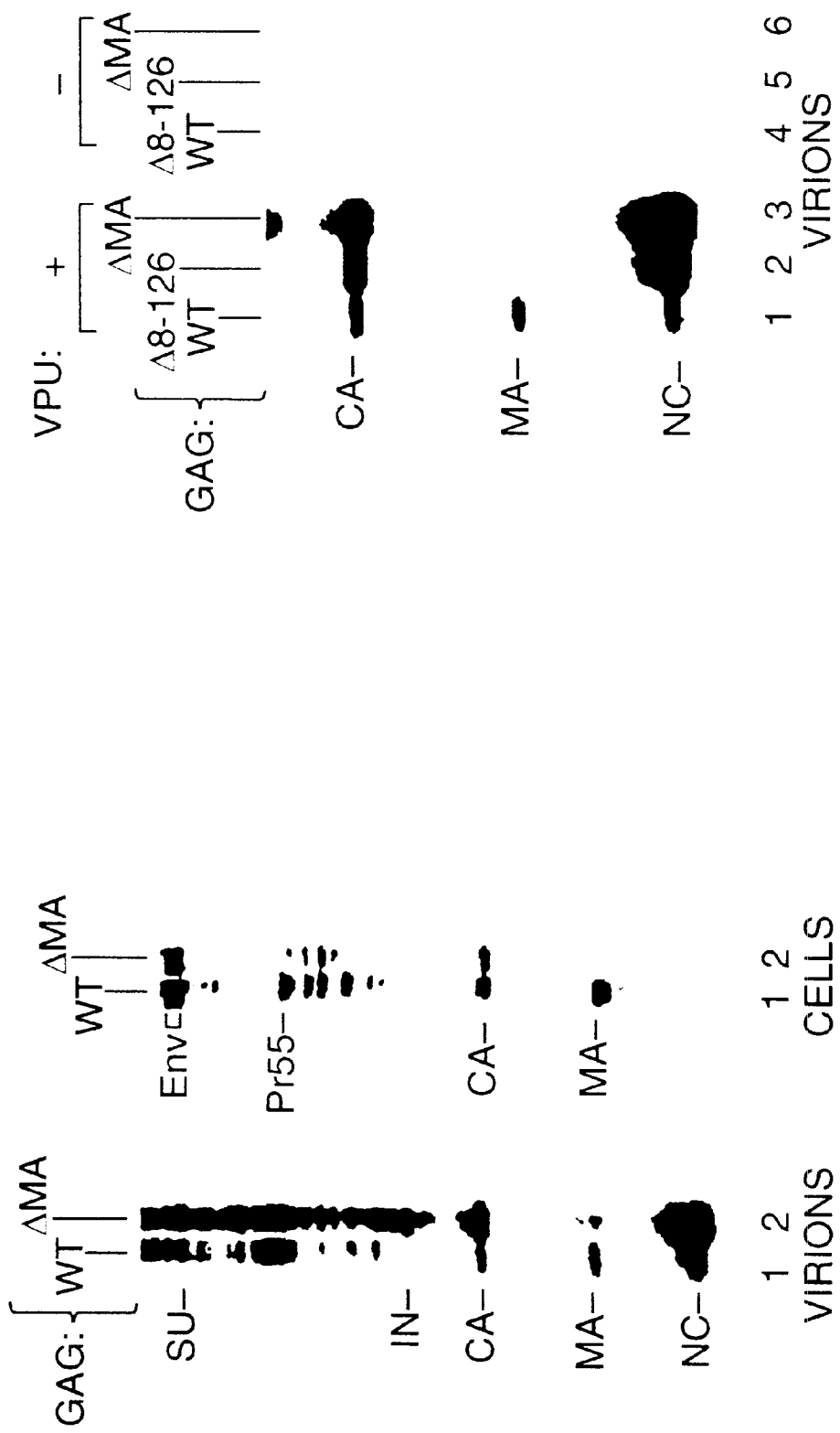
FIGS. 3A–3D show virus assembly and replication in the total absence of MA sequences.
Figure 3D:
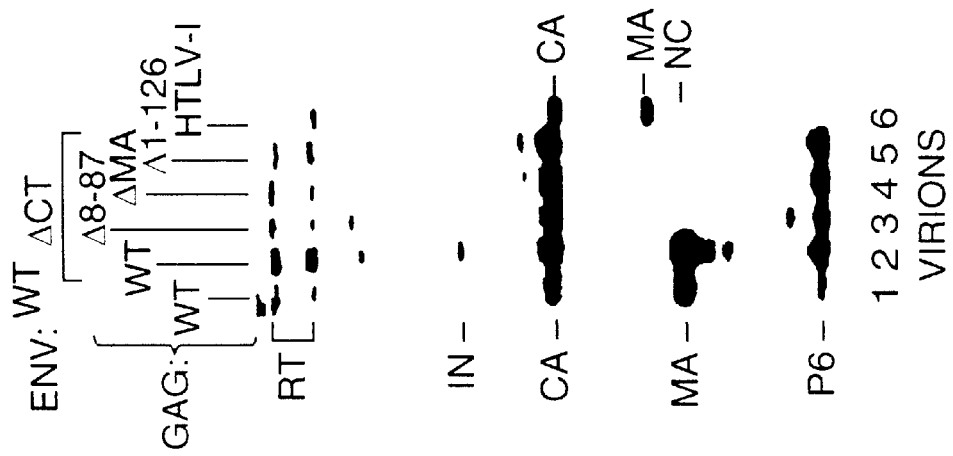

Metabolic labeling of MT4 cells with [$^{35}$S]cysteine or [$^3$H]leucine at day 5 postinfection and analysis of sucrose-purified virions by SDS-PAGE showed that the parental ΔCT construct and the Δ8-87/ΔCT mutant produced similar amounts of virus particles (FIG. 3D, lanes 2 and 3). At this early time point, MT4 cells exposed to the Δ8-126/ΔCT mutant produced significantly less virions, consistent with the delayed rise in RT activity observed for this mutant. Particles released from cells infected with the Δ8-87/ΔCT and Δ8-126/ΔCT mutants contained mature CA and NC, but lacked MA. Instead, a product which migrated considerably faster than MA was detectable in Δ8-87/ΔCT mutant particles after labeling with [$^3$H]leucine. This product was only weakly labeled, consistent with the deletion of 13 out of 14 leucine residues from MA. Accordingly, the globular core of MA is not essential for efficient HIV-1 replication in MT4 cells.

Efficient Replication in the Total Absence of MA Sequences

Since the Δ8-126/ΔCT construct retained the myristylation signal as well as sequences from the very C-terminus of MA, we examined whether it was possible to substitute all of MA with heterologous sequences while preserving the ability to form virus-like particles. To provide a heterologous myristyl anchor, we replaced the N-terminal 7 amino acids of MA in the Δ8-126/ΔCT construct with the N-terminal 9 amino acids of p60$^{v-src}$, which yielded the Δ1-126/ΔCT mutant (FIG. 1). The remaining 6 C-terminal MA residues of the Δ1-126/ΔCT mutant were replaced with the 6 residues that immediately precede protease in the HIV-1 Gag-pol fusion protein. These residues were chosen with the intention to retain a processing site at the N-terminus of the CA domain. The resulting ΔMA/ΔCT provirus in effect has the entire MA domain replaced by a heterologous 15 amino acid peptide.

Surprisingly, HeLa cells transfected with the ΔMA/ΔCT mutant released up to 10-fold more particulate Gag protein than cells transfected with the wild type provirus (FIG. 3A). Immunoprecipitation from the cell lysates indicated that the increase in particle yield was not explainable by an increase in the expression levels of the viral structural proteins (FIG. 3A). Particles produced by the ΔMA/ΔCT mutant contained equimolar amounts of CA and NC. Despite the absence of MA, the mutant particles contained significant amounts of Env protein (FIG. 3A). Equilibrium centrifugation in sucrose gradients revealed that the absence of MA did not affect particle density (data not shown). The ΔMA/ΔCT mutant clearly required an intact vpu gene for efficient particle production, indicating that MA is dispensable for the well-documented effect of Vpu on virus release (FIG. 3B).

Figure 3C:
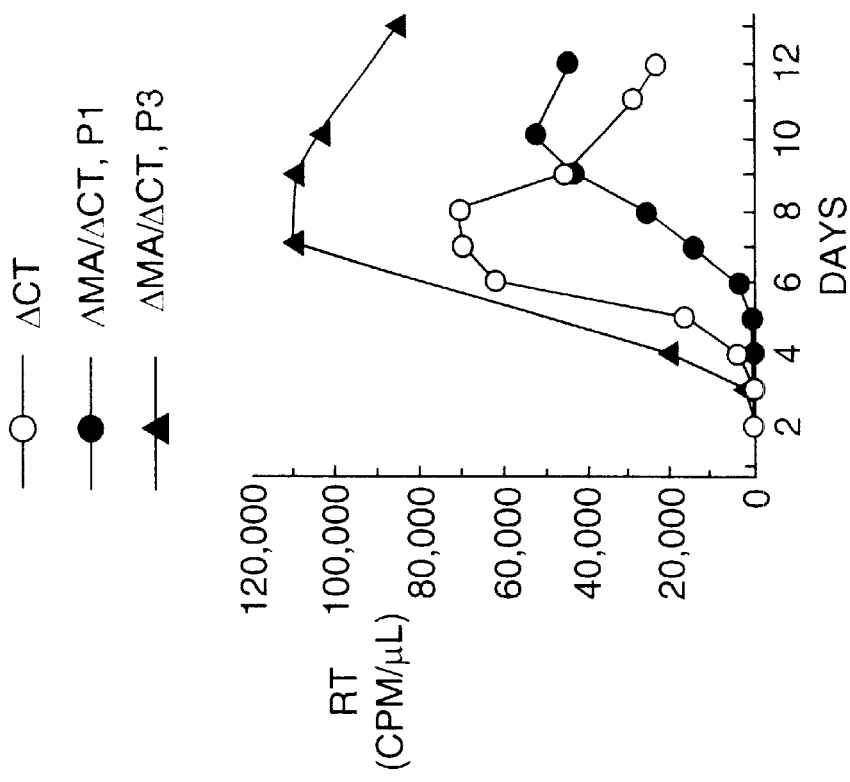
Figure 4B:
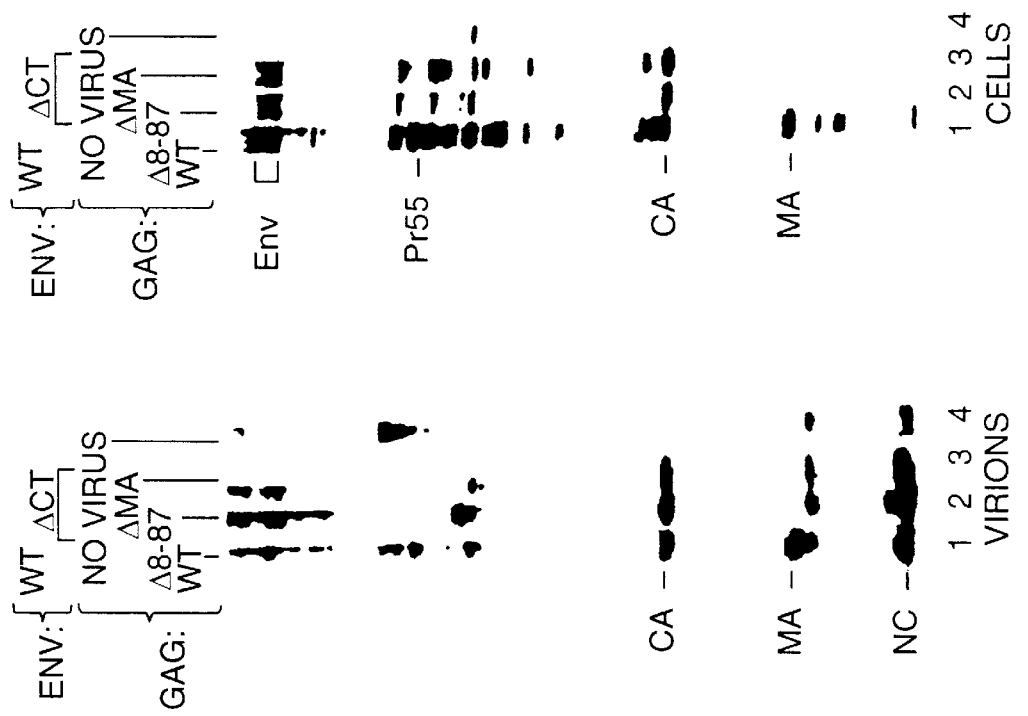
FIGS. 4A and 4B show replication of MA-deleted viruses in CEmx174 cells.
Figure 4A:
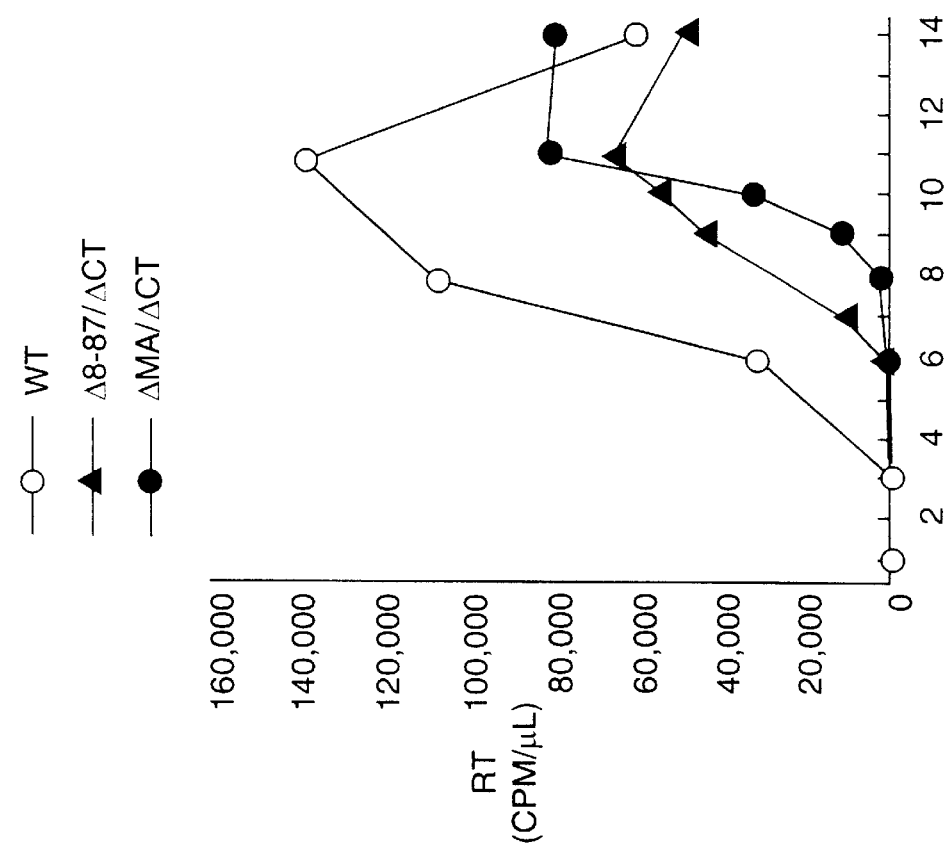

No evidence for virus replication was initially observed after exposure of MT4 cells to HeLa-derived Δ1-126/ΔCT or ΔMA/ΔCT virions. However, in some cultures RT activity began to rise rapidly between 3 and 6 weeks postinfection. Supernatant from a culture infected with the ΔMA/ΔCT mutant was harvested, normalized for RT activity, and used to infected fresh MT4 cells. The passaged virus reached peak RT levels with only a 3 day delay relative the ΔCT mutant, which indicated the emergence of a revertant. Upon further passage, accelerated replication kinetics were observed which resembled those seen with the ΔCT mutant (FIG. 3C).

The ability of the putative revertant to replicate in the absence of MA was verified by metabolic labeling of infected MT4 cells with [$^3$H]leucine. Cells infected with the passaged virus released particles which contained the mature Gag products CA and p6 as well as the pol-encoded products RT and IN in similar relative molar amounts as wild type HIV-1 virions (FIG. 3D, lane 4). NC, which lacks leucine residues, was detected in equimolar amounts relative to CA after metabolic labeling with [$^{35}$S]cysteine (data not shown). MA was clearly absent from particles produced by the passaged ΔMA/ΔCT virus (FIG. 3D, lane 4). Similar results were obtained with passaged virus derived from MT4 cells that had been infected with the Δ1-126/ΔCT mutant (FIG. 3D, lane 5). A comparison with the protein profile of HTLV-1 virions produced by MT2 cells ruled out the possibility that the MA protein of HTLV-1 compensated for that of HIV-1 (FIG. 3D, lane 6). This result was anticipated, because MT4 cells, although transformed with HTLV-1, do not produce HTLV-1 particles.

Electron Microscopic Analysis of Infected Cells

Figure 5A:
FIGS. 5A–5C show thin-section electron microscopy of infected MT4 cell cultures.
Figure 5B:
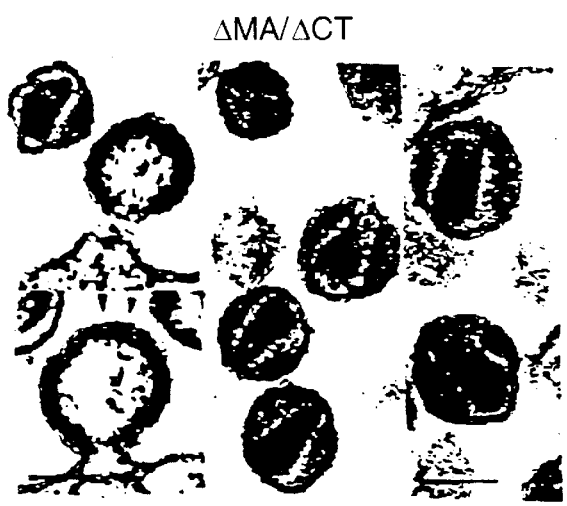
Figure 5C:
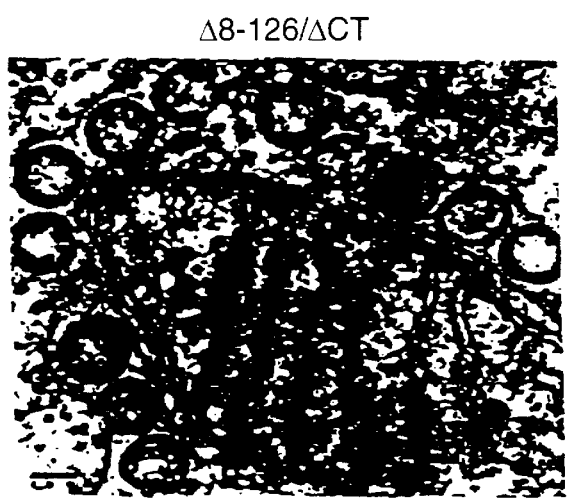

To analyze the morphology of particles lacking MA, infected MT4 cells were examined by transmission electron microscopy. Cultures infected with the passaged ΔMA/ΔCT virus showed numerous, roughly spherical extracellular particles with a central electron-dense core. The particles, which resembled wild type HIV-1 virions, were covered by a lipid envelope. Occasionally, projections which presumably represented Env glycoprotein spikes were visible on their surface. Appropriate sections showed cone-shaped cores which extended across the entire diameter of the virion, as is typical for HIV-1. However, aberrant core structures appeared more frequent than in wild type particles. While a few grossly enlarged circular structures with multiple cores were seen, MA-less particles which contained a single core had an average diameter (143±20 nm; n=56) that was comparable to that of particles produced by the parental ΔCT virus (155±16 nm; n=44). In cells infected with the MA-less mutant, budding occurred both at the plasma membrane and into the endoplasmic reticulum (FIGS. 5A–5C), consistent with reports that alterations in MA can cause a redirection of assembly to intracellular membrane compartments. Particles in the endoplasmic reticulum frequently seemed arrested at a late step of budding and remained immature, as has been observed previously. Budding structures, both at the cell membrane and in the endoplasmic reticulum, as well as mature extracellular particles with a morphology similar to that of wild type HIV-1 were also observed in cultures infected with the Δ8-87/ΔCT and Δ8-126/ΔCT mutants (FIG. 5C, and data not shown).

Isolation of Replication-Competent Proviruses Lacking MA Coding Sequences

After 3 passages of the ΔMA/ΔCT virus in MT4 cells, DNA was extracted and used as a template for PCR amplification of HIV-1 sequences. PCR fragments were then substituted for the homologous regions of the ΔMA/ΔCT provirus. A recombinant clone designated R0, constructed from PCR fragments which included the gag and pol genes, yielded virus that replicated with similar kinetics as the ΔCT mutant. DNA sequence analysis revealed that the R0 provirus retained the ΔMA mutation, except for a change which resulted in a Phe to Val substitution at position 12 of the 14-amino-acid peptide introduced to replace MA. Other mutations in gag changed the codon for Met68 of CA to a codon specifying Val, and the codon for Arg 32 of NC to a codon specifying Lys. Additionally, the R0 recombinant contained point mutations in pol. To determine which of these mutations were critical for the revertant phenotype, appropriate segments from the R0 recombinant were transferred to the corresponding position of the MA/ΔCT provirus. Virus stocks were then produced by transfection of HeLa cells and used to infect MT4 cells after normalization for RT activity.

Figure 6A:
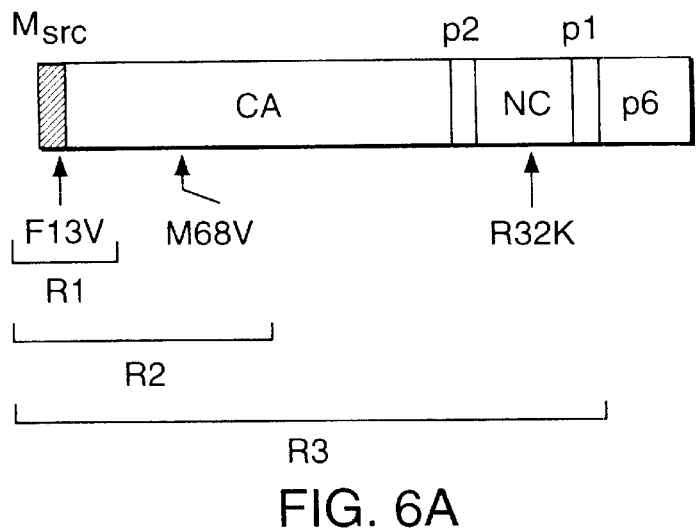
FIGS. 6A–6C show characterization of compensatory mutations which allow efficient HIV-1 replication in MT4 cells in the total absence of MA sequences.
Figure 6B:
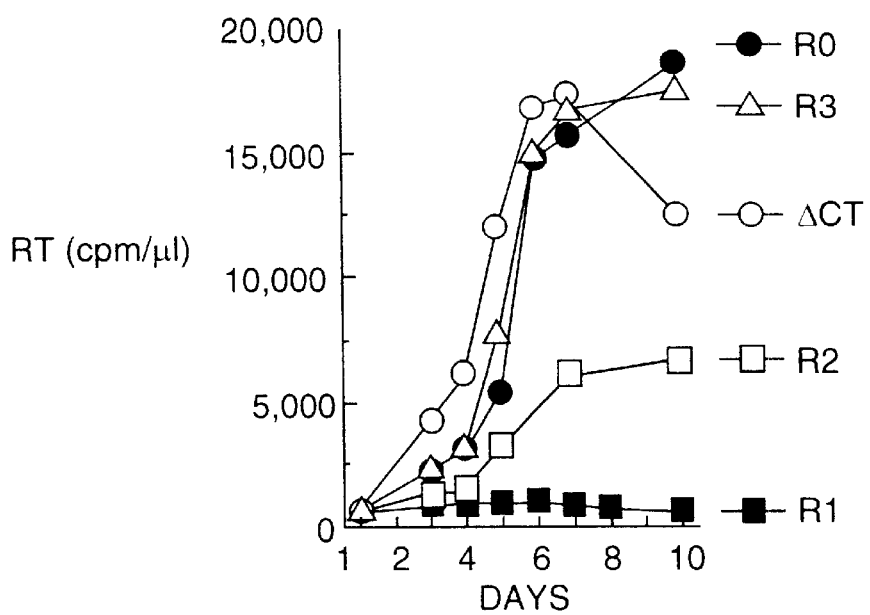
Figure 6C:
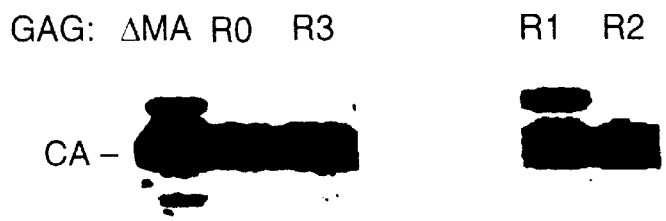

The R1 recombinant, which harbored only the Phe to Val change in a ΔMA/ΔCT background, did not yield a spreading infection in MT4 cells (FIGS. 6A–6C). In contrast, the R2 recombinant, which contained the Phe Val change together with the Met68 Val change in CA, replicated with only moderately delayed kinetics relative to the original R0 recombinant. Finally, the R3 recombinant, which additionally contained the Arg32 Lys change in NC, replicated as well as the R0 recombinant (FIGS. 6A–6C).

The location of the Phe Val change suggested that it may have been selected to improve processing at the N-terminus of CA. Consistent with this possibility, transfection into HeLa cells showed that virions produced by the parental ΔMA/ΔCT mutant contained significantly more of a product which migrated just above CA than virions produced by the R0 and R3 recombinants (FIG. 6C). The electrophoretic mobility of this product, which was not present in wild type virions, indicated that it represented an incompletely processed form of CA which had the 15-amino-acid$_{[src]}$MA peptide attached to its N-terminus. Surprisingly, virions produced by the R1 recombinant, which harbors only the Phe to Val change, contained even more of this product. However, virions produced by the R2 recombinant, which additionally harbors the Met68 Val change in CA, contained almost exclusively fully processed CA (FIG. 6C). Interestingly, a second, independently obtained revertant also contained the Phe to Val change as well as a Pro147 to Thr change in CA, which had a similar effect on CA processing as the Met68 to Val change (data not shown). These results suggest that the changes in CA may have allowed virus replication by facilitating processing between the heterologous myristyl anchor and CA.

Efficient Infection of T Cell Lines and Primary Cells in the Absence of the Globular Head of MA The ΔCT mutation, which was necessary to restore Env incorporation into MA mutant particles, severely restricts the host cell tropism of HIV-1. However, a single-cycle infection assay revealed that the cytoplasmic tail truncation does not significantly affect the early phase of virus transmission in several T cell lines which cannot be productively infected by this mutant (data not shown). This assay uses recombinant viruses produced by cotransfection of pHXBH10 envCAT together with an Env expression construct. The pHXBH10 envCAT plasmid contains an HIV-1 provirus with a deletion in env and a gene encoding chloramphenicol acetyltransferase (CAT) in place of the nef gene. The infectivity of recombinant viruses is assessed by measuring CAT activity in target cells.

To further examine the efficiency of the early phase of infection in the absence of the globular head of MA, a variant of pHXBH10 envCAT which carries the Δ8-87 mutation was constructed. This variant, or its wild type counterpart, was transfected into HeLa cells together with pEnv$_{HXB}$ΔCT, an expression vector for C-terminally truncated HIV-1 Env. Alternatively, the vesicular stomatitis virus (VSV) G glycoprotein, which has only a short cytoplasmic domain, was provided in trans. Recombinant virus released from the transfected cells was normalized for RT activity and used to infect a variety of target cells. The Δ8-87 mutation reduced the transfer of CAT activity to MT4 cells by about threefold, indicating that the deletion in MA had only a minor effect on a single round of virus transmission in these cells (FIG. 7A). Similarly, the Δ8-87 mutation had little or no effect on the expression of CAT activity in the T cell lines C8166, SupT1, CEM-SS, and Jurkat, regardless of whether truncated HIV-1 Env protein or VSV G protein were used (FIG. 7B, and data not shown). In mitogen-stimulated PBMC, Δ8-87 mutant particles yielded approximately four-fold less CAT activity than wild type particles when complemented with C-terminally truncated HIV-1 Env, but retained full infectivity when pseudotyped with VSV G (data not shown).

We introduced the ΔCT mutation into an expression construct for the Env proteins of the macrophage-tropic primary HIV-1 isolate ADA. MDM were then exposed to recombinant viruses containing ADA Env. As shown in FIG. 7C, the Δ8-87 mutation reduced the efficiency of infection of MDM about fifteen-fold. As expected, hardly any CAT activity was detectable following exposure of MDM to recombinant viruses containing T cell-adapted rather than macrophage-tropic HIV-1 Env. Interestingly, pseudotyping with VSV G protein completely suppressed the defect caused by the Δ8-87 mutation and allowed efficient infection of MDM in the absence of the globular head of MA (FIGS. 7C and 7D). This finding was reproducible with MDM from several different donors. The observed CAT activity was reduced to background levels when infections were carried out in the presence of 5 $\mu$M azidothymidine (data not shown). Furthermore, the transfer of CAT activity to MDM was blocked by a single amino acid substitution in integrase (Asp116 to Ala) which is known to destroy integrase activity. These results indicate that the globular head of MA, which contains the reported NLS, is dispensable for reverse transcription and integration in MDM.

Replication in Other Cell Lines

In an attempt to overcome the host restriction imposed by the ΔCT mutation, MT4 cells infected with the Δ8-87/ΔCT or the ΔMA/ΔCT mutant were cocultivated with CEMx174 cells. Despite the inability of the parental ΔCT mutant to productively infect CEMx174 cells (data not shown), the cocultures eventually yielded virus which could be serially passaged in these cells. To examine the efficiency of virus replication, virus stocks obtained from infected CEMx174 cells were normalized for RT activity and used to infect fresh CEMx174 cells. Compared to wild type virus, the passaged Δ8-87/CT and ΔMA/ΔCT mutants replicated with somewhat delayed kinetics, but eventually produced high levels of RT activity (FIG. 4A). Jurkat cells exposed to CEMx174-derived Δ8-87/ΔCT virus also produced high levels of RT activity after a two-week delay relative to a parallel culture infected with wild type virus (data not shown).

PCR amplification of gag sequences verified the presence of MA-deleted viral DNA after several passages in CEMx174 cells (data not shown). To further confirm that the observed increases in RT activity reflected HIV-1 replication, infected CEMx174 cells were metabolically labeled with [$^{35}$S]cysteine. FIG. 4B shows that CEMx174 cells exposed to the passaged Δ8-87/ΔCT or ΔMA/ΔCT mutant released particles which contained CA and NC but lacked MA. Moreover, in addition to CA, a shortened Gag precursor of the expected size was detectable in the infected cells. Of note, the mutants also produced a shortened Env precursor, indicating that compensatory changes had occurred which allowed virus replication in CEMx174 cells in the absence of both MA and Env cytoplasmic tail sequences.

REFERENCES

1. Aiken, C. (1997). J. Virol. 71, 5871–5877.
2. Bryant, M., and Ratner, L. (1990). Proc. Natl. Acad. Sci. USA 87, 523–527.
3. Buchschacher, G. L., and Panganiban, A. T. (1992). J. Virol. 66, 2731–2739.
4. Bukrinskaya, A. G., Ghorpade, A., Heinzinger, N. K., Smithgall, T. E., Lewis, R. E., and Stevenson, M. (1996). Proc. Natl. Acad. Sci. USA 93, 367–371.
5. Bukrinsky, M. I., Sharova, N., Dempsey, M. P., Stanwick, T. L., Bukrinskaya, A. G., Haggerty, S., and Stevenson, M. (1992). Proc. Natl. Acad. Sci. USA 89, 6580–6584.

6. Bukrinsky, M. I., Haggerty, S., Dempsey, M. P., Sharova, N., Adzhubel, A., Spitz, L., Lewis, P., Goldfarb, D., Emerman, M., and Stevenson, M. (1993). Nature 365, 666–669.
7. Christensen, A. M., Massiah, M. A., Turner, B. G., Sundquist, W. I., and Summers, M. F. (1996). J. Mol. Biol. 264, 1117–1131.
8. Freed, E. O., Orenstein, J. M., Buckler-White, A. J., and Martin, M. A. (1994). J. Virol. 68, 5311–5320.
9. Freed, E. O., Englund, G., and Martin, M. A. (1995). J. Virol. 69, 3949–3954.
10. Freed, E. O., and Martin, M. A. (1995). J. Virol. 69, 1984–1989.
11. Freed, E. O., Englund, G., Maldarelli, F., and Martin, M. A. (1997). Cell 88, 171–174.
12. Gallay, P., Swingler, S., Aiken, C., and Trono, D. (1995a). Cell 80, 379–388.
13. Gallay, P., Swingler, S., Song, J., Bushman, F., and Trono, D. (1995b). Cell 83, 569–576.
14. Gallay, P., Hope, T., Cin, D., and Trono, D. (1997). Proc. Natl. Acad. Sci. USA 94, 9825–9830.
15. Conte, M. R., Klikova, M., Hunter, E., Rumi, T., and Matthews, S. (1997). EMBO J. 16, 5819–5826.
16. Cosson, P. (1996). EMBO J. 15, 5783–5788.
17. Dorfman, T., Mammano, F., Haseltine, W. A., and Göttlinger, H. G. (1994). J. Virol. 68, 1689–1696.
18. Dubay, J. W., Roberts, S. J., Hahn, B. H., and Hunter, E. (1992). J. Virol. 66, 6616–6625.
19. Fäcke, M., Janetzko, A., Shoeman, R. L., and Kräusslich, H.-G. (1993). J. Virol. 67, 4972–4980.
20. Fouchier, R. A. M., Meyer, B. E., Simon, J. H. M., Fischer, U., and Malim, M. H. (1997). EMBO J. 16, 4531–4539.
21. Gelderblom, H. R. (1991). AIDS 5, 617–638.
22. Göttlinger, H. G., Sodroski, J. G., and Haseltine, W. A. (1989). Proc. Natl. Acad. Sci. USA 86, 5781–5785.
23. Heinzinger, N. K., Bukrinsky, M. I., Haggerty, S. A., Ragland, A. M., Kewalramani, V., Lee, M.-A., Gendelman, H. E., Ratner, L., Stevenson, M., and Emerman, M. (1994). Proc. Natl. Acad. Sci. USA 91, 7311–7315.
24. Helseth, E., Kowalski, M., Gabuzda, D., Olshevsky, U., Haseltine, W., and Sodroski, J. (1990). J. Virol. 64, 2416–2420.
25. Hill, C. P., Worthylake, D., Bancroft, D. P., Christensen, A. M., and Sundquist, W. I. (1996). Proc. Natl. Acad. Sci. USA 93, 3099–3104.
26. Hunter, E. (1994). Semin. Virol. 5, 71–83.
27. Kräusslich, H.-G., and Welker, R. (1996). Curr. Top. Microbiol. Immunol. 214, 25–63.
28. Lee, P. P., and Linial, M. L. (1994). J. Virol. 68, 6644–6654.
29. Lee, Y.-H., Schwartz, M. D., and Paganiban, A. T. (1997). Virology 237, 46–55.
30. Lewis, P., Hensel, M., and Emerman, M. (1992). EMBO J. 8, 3053–3058.
31. Mammano, F., Kondo, E., Sodroski, J., Bukovsky, A., and Göttlinger, H. G. (1995). J. Virol. 69, 3824–3830.
32. Massiah, M. A., Starich, M. R., Paschall, C., Summers, M. F., Christensen, A. M., and Sundquist, W. I. (1994). J. Mol. Biol. 244, 198–223.
33. Matthews, S., Barlow, P., Boyd, J., Barton, G., Russell, R., Mills, H., Cunningham, M., Meyers, N., Burns, N., Clark, N., Kingsman, S., Kingsman, A., and Campbell, I. (1994). Nature 370, 666–668.
34. Nelle, T. D., and Wills, J. W. (1996). J. Virol. 70, 2269–2276.
35. Parent, L. J., Wilson, C. B., Resh, M. D., and Wills, J. W. (1996). J. Virol. 70, 1016–1026.
36. Saggioro, D., Panozzo, M., and Chieco-Bianchi, L. (1990). Cancer Res. 50, 4968–4973.
37. Stein, B. S., Gowda, S. D., Lifson, J. d., Penhallow, R. C., Bensch, K. G., and Engleman, e.g. (1987). Cell 49, 659–668.
38. von Schwedler, U., Kornbluth, R. S., and Trono, D. (1994). Proc. Natl. Acad. Sci. USA 91, 6992–6996.
39. Wang, C.-T., Zhang, Y., McDermott, J., and Barklis, E. (1993). J. Virol. 67, 7067–7076.
40. Weinberg, J. B., Matthews, T. J., Cullen, B. R., and Malim, M. H. (1991). J. Exp. Med. 174, 1477–1482.
41. Wilk, T., Pfeiffer, T., and Bosch, V. (1992). Virology 189, 167–177.
42. Willey, R. L., Smith, D. H., Lasky, L. A., Theodore, T. S., Earl, P. L., Moss, B., Capon, D. J., and Martin, M. A. (1988). J. Virol. 62, 139–147.
43. Wiskerchen, M., and Muesing, M. A. (1995). J. Virol. 69, 376–386.
44. Yee, J.-K., Friedmann, T., and Burns, J. C. (1994). Methods Cell Biol. 43, 99–112.
45. Yu, X., Yu, Q.-C., Lee, T.-H., and Essex, M. (1992a). J. Virol. 66, 5667–5670.
46. Yu, X., Yuan, X., Matsuda, Z., Lee, T.-H., and Essex, M. (1992b). J. Virol. 66, 4966–4971.
47. Zhou, W., Parent, L. J., Wills, J. W., and Resh, M. D. (1994). J. Virol. 68, 2556–2569.
48. Zhou, W., and Resh, M. D. (1996). J. Virol. 70, 8540–8548.

All the references described herein are incorporated by reference.

What is claimed:

1. A lentiviral vector system comprising:
   (a) a first vector, referred to as a pol vector, comprising a nucleotide sequence encoding a lentiviral pol protein, operably linked to a promoter and a polyadenylation sequence;
   (b) a nucleotide sequence encoding a lentiviral gag protein wherein at least 25% of the lentiviral matrix (MA) protein has been deleted, and wherein the MA myristylation sequence is present or substituted by a heterologous myristylation sequence, operably linked to a promoter and a polyadenylation sequence, referred to as gag nucleotide sequence and the gag nucleotide sequence is present on the pol vector or a different vector, referred to as a vector the gag nucleotide sequence is present on;
   (c) another vector, referred to as the env vector, comprising a nucleotide sequence to encode a functional env gene, operably linked to a promoter and a polyadenylation sequence, wherein if said env protein is a lentiviral env protein, it lacks at least 50% of the cytoplasmic tail or if it is not a lentiviral env protein it is an env protein of an endocytic virus;
   wherein the pol vector, the vector the gag nucleotide sequence is present on and the envelope vector, when expressed in combination, form a MA-deleted virion containing an envelope protein around a lentiviral capsid; and
   wherein said pol vector, the vector gag nucleotide sequence is present on and the env vector do not contain a sufficient number of nucleotides to encode the lentiviral gag, env and pol proteins on a single vector and do not contain nucleotides of the genome to effectively package HIV RNA, referred to as a packaging segment.

2. The vector system of claim 1, wherein said nucleotide sequences encoding the gag and pol proteins are within the same vector.

3. The vector system of claim 1, wherein said nucleotide sequences encoding the gag and pol proteins are within separate vectors.

4. The lentiviral vector system of claim 1, further comprising another vector containing a gene of interest operably linked to a promoter and a lentiviral packing sequence necessary to package the lentiviral RNA into the lentiviral virions.

5. The lentiviral vector system of claim 1, wherein the lentiviral pol protein and the lentiviral gag protein is from a primate lentivirus, a feline immunodeficiency virus (FIV), a visna virus, or an equine infectious anemia virus.

6. The lentiviral vector system of claim 2, wherein the lentiviral pol protein and the lentiviral gag protein is from a primate lentivirus, a feline immunodeficiency virus (FIV), a visna virus, or an equine infectious anemia virus.

7. The lentiviral vector system of claim 3, wherein the lentiviral pol protein and the lentiviral gag protein is from a primate lentivirus, a feline immunodeficiency virus (FIV), a visna virus, or an equine infectious anemia virus.

8. The lentiviral vector system of claim 4, wherein the lentiviral pol protein and the lentiviral gag protein is from a primate lentivirus, a feline immunodeficiency virus (FIV), a visna virus, or an equine infectious anemia virus.

9. The lentiviral vector system of claim 5, wherein the lentiviral pol protein and the lentiviral gag protein is from a primate lentivirus selected from a human immunodeficiency virus (HIV) or a simian immunodeficiency virus (SIV).

10. The lentiviral vector system of claim 5, wherein the lentivirus is FIV.

11. The lentiviral vector system of claim 6, wherein the lentiviral pol protein and the lentiviral gag protein is from a primate lentivirus selected from a human immunodeficiency virus (HIV) or a simian immunodeficiency virus (SIV).

12. The lentiviral vector system of claim 6, wherein the lentivirus is FIV.

13. The lentiviral vector system of claim 7, wherein the lentiviral pol protein and the lentiviral gag protein is from a primate lentivirus selected from a human immunodeficiency virus (HIV) or a simian immunodeficiency virus (SIV).

14. The lentiviral vector system of claim 7, wherein the lentivirus is FIV.

15. The lentiviral vector system of claim 8, wherein the lentiviral pol protein and the lentiviral gag protein is from a primate lentivirus selected from a human immunodeficiency virus (HIV) or a simian immunodeficiency virus (SIV).

16. The lentiviral vector system of claim 8, wherein the lentivirus is FIV.

17. A lentiviral vector system comprising:
(a) a first vector, referred to as pol vector, comprising a nucleotide sequence encoding an HIV pol protein, operably linked to a promoter and a polyadenylation sequence;
(b) a nucleotide sequence encoding an HIV gag protein wherein at least 25% of the HIV matrix protein has been deleted, and wherein the MA myristylation sequence is present or substituted by a heterologous myristylation sequence operably linked to a promoter and a polyadenylation sequence, referred to as gag nucleotide sequence and said gag nucleotide sequence is present on the pol vector or a different vector referred to as a vector the gag nucleotide sequence is present on;
(c) a second vector, referred to as the env vector, comprising a nucleotide sequence to encode a functional env gene, operably linked to a promoter and a polyadenylation sequence, wherein if said env protein is an HIV env protein, it lacks at least 50% of the cytoplasmic tail or if it is not an HIV env protein it is an env protein, of an endocytic virus;
wherein the pol vector, the vector said gag nucleotide sequence is present on and the envelope vector, when expressed in combination, form a MA-deleted virion containing an envelope protein around an HIV capsid; and
wherein the pol vector, the envelope vector the gag nucleotide sequence is present on, and the envelope vector do not contain sufficient number of nucleotides to encode the HIV gag, env and pol proteins on a single vector and do not contain nucleotides of the genome to effectively package HIV RNA referred to as a packaging segment.

18. The lentiviral vector system of claim 17, wherein said gag nucleotide sequence is present on said pol vector.

19. The lentiviral vector system of claim 17, wherein said gag nucleotide sequence is on a different vector than the pol vector.

20. The lentiviral vector system of claim 17, further comprising a vector containing a gene of interest operably linked to a promoter and a HIV packing sequence necessary to package the HIV RNA into virions.

21. A method of transferring a gene of interest to a host cell comprising transfecting said host cell with the vector system of claim 17.

22. The lentiviral vector system of claim 17, wherein said HIV gag and pol are from the HIV-1 genome.

23. A lentiviral vector system comprising:
(a) a first vector, referred to as pol vector, comprising a nucleotide sequence encoding an HIV, SIV or FIV pol protein, operably linked to a promoter and a polyadenylation sequence;
(b) a nucleotide sequence encoding an HIV, SIV or FIV gag protein wherein at least 25% of the HIV matrix protein has been deleted, and wherein the MA myristylation sequence is present or substituted by a heterologous myristylation sequence operably linked to a promoter and a polyadenylation sequence, referred to as gag nucleotide sequence and said gag nucleotide sequence is present on the pol vector or a different vector, referred to as vector the gag nucleotide sequence is present on;
(c) a second vector, referred to as the env vector, comprising a nucleotide sequence to encode a functional env gene, operably linked to a promoter and a polyadenylation sequence, wherein if said env protein is an HIV, SIV or FIV env protein, it lacks at least 50% of the cytoplasmic tail or if it is not an HIV, SIV or FIV env protein it is an env protein of an endocytic virus;
wherein the pol vector, the vector the gag nucleotide sequence is present on and the envelope vector, when expressed in combination, form a MA-deleted virion containing an envelope protein around an HIV, SIV or FIV capsid; and
wherein the pol vector, the vector the gag nucleotide sequence is present on and the envelope vector do not contain sufficient number of nucleotides to encode the HIV, SIV or FIV gag, env and pol proteins on a single vector and do not contain nucleotides of the genome to effectively package HIV, SIV or FIV RNA referred to as a packaging segment.

24. The lentiviral vector system of claim 23, wherein said gag nucleotide sequence is present on the pol vector.

25. The lentiviral vector system of claim 23, wherein said gag nucleotide sequence is on a different vector than the pol vector.

26. The lentiviral vector system of claim 23, further comprising another vector containing a gene of interest operably linked to a promoter and a lentiviral packing sequence necessary to package the lentiviral RNA into lentiviral virions.

* * * * *

SEQUENCE LISTING

<160> NUMBER OF SEQ ID NOS: 11

<210> SEQ ID NO 1
<211> LENGTH: 8
<212> TYPE: PRT
<213> ORGANISM: Rous sarcoma virus

<400> SEQUENCE: 1

Gly Ser Ser Lys Ser Lys Pro Lys
1               5

<210> SEQ ID NO 2
<211> LENGTH: 74
<212> TYPE: DNA
<213> ORGANISM: Homo sapiens

<400> SEQUENCE: 2
ggaggctaga aggagagaga tgggtagcag caagagcaag cctaagtcta gagggggaga    60
attagatcga tggg    74

<210> SEQ ID NO 3
<211> LENGTH: 15
<212> TYPE: PRT
<213> ORGANISM: Homo sapiens

<400> SEQUENCE: 3

Met Gly Ser Ser Lys Ser Lys Pro Lys Thr Val Ser Phe Asn Phe
1               5                   10                  15

<210> SEQ ID NO 4
<211> LENGTH: 88
<212> TYPE: DNA
<213> ORGANISM: Homo sapiens

<400> SEQUENCE: 4
ggaggctaga aggagagaga tgggtagcag caagagcaag cctaagacag taagctttaa    60
tttccctata gtgcagaaca tccagggg    88

<210> SEQ ID NO 5
<211> LENGTH: 23
<212> TYPE: DNA
<213> ORGANISM: Homo sapiens

<400> SEQUENCE: 5
caatacatac cgcgaatggc agc    23

<210> SEQ ID NO 6
<211> LENGTH: 18
<212> TYPE: DNA
<213> ORGANISM: Homo sapiens

<400> SEQUENCE: 6
gacgcaggac tcggcttg    18

<210> SEQ ID NO 7
<211> LENGTH: 28
<212> TYPE: DNA
<213> ORGANISM: Homo sapiens

<400> SEQUENCE: 7
tagctttatg tccacagatt tctatgag    28

<210> SEQ ID NO 8
<211> LENGTH: 29
<212> TYPE: DNA
<213> ORGANISM: Homo sapiens

<400> SEQUENCE: 8
tctattagat acaggagcag atgatacag    29

<210> SEQ ID NO 9
<211> LENGTH: 25
<212> TYPE: DNA

```
<213> ORGANISM: Homo sapiens

<400> SEQUENCE: 9
gctctagtct aggatctact ggctc                                    25

<210> SEQ ID NO 10
<211> LENGTH: 23
<212> TYPE: DNA
<213> ORGANISM: Homo sapiens

<400> SEQUENCE: 10
ggatacttgg gcaggagtgg aag                                      23

<210> SEQ ID NO 11
<211> LENGTH: 24
<212> TYPE: DNA
<213> ORGANISM: Homo sapiens

<400> SEQUENCE: 11
tcccttgtag caagctcgat gtca                                     24
```